(12) United States Patent
Sawa et al.

(10) Patent No.: US 7,960,139 B2
(45) Date of Patent: Jun. 14, 2011

(54) ALKYNYL SUGAR ANALOGS FOR THE LABELING AND VISUALIZATION OF GLYCOCONJUGATES IN CELLS

(75) Inventors: Masaaki Sawa, Ibaraki (JP); Chi-Huey Wong, Taipei (TW); Tsui-Ling Hsu, Taipei (TW); Sarah Hanson, San Marcos, CA (US)

(73) Assignee: Academia Sinica, Taipei (TW)

( * ) Notice: Subject to any disclaimer, the term of this patent is extended or adjusted under 35 U.S.C. 154(b) by 442 days.

(21) Appl. No.: 12/079,226

(22) Filed: Mar. 24, 2008

(65) Prior Publication Data

US 2008/0268468 A1    Oct. 30, 2008

Related U.S. Application Data

(60) Provisional application No. 60/896,777, filed on Mar. 23, 2007.

(51) Int. Cl.
*G01N 33/53* (2006.01)
(52) U.S. Cl. .............................. 435/41; 435/7.1; 435/7.2
(58) Field of Classification Search ........................ None
See application file for complete search history.

(56) References Cited

U.S. PATENT DOCUMENTS 5,625,124 A * 4/1997 Falk et al. .......................... 800/3

OTHER PUBLICATIONS

Hsu TL, Hanson SR, Kishikawa K, Wang SK, Sawa M, Wong CH, Alkynyl sugar analogs for the labeling and visualization of glycoconjugates in cells, (2007) Proc Natl Acad Sci 104:2614-2619.
Varki A, Cummings R, Esko JD, Freeze H, Hart GW, Marth J (1999) in Essentials of Glycobiology (Cold Spring Harbor Lab Press, Cold Spring Harbor, NY), pp. 1-635.
Axford JS, Glycosylation and rheumatic disease, (1999) Biochim Biophys Acta 1455:219-229.
Dube, D. H. & Bertozzi, C. R., Glycans in cancer and inflammation—potential for therapeutics and diagnostics, (2005) Nat. Rev. Drug Discov. 4, 477-488.
Mackiewicz A, Mackiewicz K, Glycoforms of serum a1-acid glycoprotein as markers of inflammation and cancer, (1995) Glycoconj J 12:241-247.
Meezan E, Wu HC, Black PH, Robbins PW, Comparative Studies on the Carbohydrate-Containing Membrane Components of Normal and Virus-Transformed Mouse Fibroblasts. II. Separation of Glycoproteins and Glycopeptides by Sephadex Chromatography*, (1969) Biochemistry 8:2518-2524.
Turner GA, N-Glycosylation of serum proteins in disease and its investigation using lectins, (1992) Clin Chim Acta 208:149-171.
Orntoft TF, Vestergaard EM, Clinical aspects of altered glycosylation of glycoproteins in cancer, (1999) Electrophoresis 20:362-371.
Sell S, Cancer-Associated Carbonhydrates Identified by Monoclonal Antibodies, (1990) Hum Pathol 21:1003-1019.
Taylor-Papadimitriou J, Epenetos AA, Exploiting altered glycosylation patterns in cancer: progress and challenges in diagnosis and therapy, (1994) Trends Biotechnol 12:227-233.
Zhang S, Cordon-Cardo C, Zhang HS, Reuter VE, Adluri S, Hamilton WB, Lloyd KO, Livingston PO, Selection of tumor antigens as targets for immune attack using immunohistochemistry: I. Focus on gangliosides, (1997) Int J Cancer 73:42-49.
Zhang S, Zhang HS, Cordon-Cardo C, Reuter VE, Singhal AK, Lloyd KO, Livingston PO, Selection of tumor antigens as targets for immune attack using immunohistochemistry: II. Blood group-related antigens, (1997) Int J Cancer 73:50-56.
Mahal LK, Yarema KJ, Bertozzi CR, Engineering Chemical Reactivity on Cell Surfaces Through Oligosaccharide Biosynthesis, (1997) Science 276:1125-1128.
Tai HC, Khidekel N, Ficarro SB, Peters EC, Hsieh-Wilson LC, Parallel Identification of O-GlcNAc-Modified Proteins from Cell Lysates, (2004) J Am Chem Soc 126:10500-10501.
Saxon E, Bertozzi CR, Cell Surface Engineering by a Modified Staudinger Reaction, (2000) Science 287:2007-2010.
Sampathkumar SG, Li AV, Jones MB, Sun Z, Yarema KJ, Metabolic installation of thiols into sialic acis modulates adhesion and stem cell biology, (2006) Nat Chem Biol 2:149-152.
Agard NJ, Baskin JM, Prescher JA, Lo A, Bertozzi CR, A Comparative Study of Bioorthogonal Reactions with Azides, (2006) ACS Chem Biol 1:644-648.
Agard NJ, Prescher JA, Bertozzi CR, A Strain-Promoted [3 + 2] Azide-Alkyne Cycloaddition for Covalent Modification of Biomolecules in Living Systems, (2004) J Am Chem Soc 126:15046-15047.
Rabuka D, Hubbard SC, Laughlin ST, Argade SP, Bertozzi CR, A Chemical Reporter Strategy to Probe Glycoprotein Fucosylation, (2006) J Am Chem Soc 128:12078-12079.
Sawa M., Hsu T. L., Itoh T., Sugiyama M., Hanson S. R. , Vogt P. K. , Wong C. H. , Glycoproteomic probes for fluorescent imaging of fucosylated glycansin vivo, (2006) Proc. Natl. Acad. Sci. USA 103, 12371-12376.
Dube DH, Prescher JA, Quang CN, Bertozzi CR, Probing mucin-type O-linked glycosylation in living animals, (2006) Proc Natl Acad Sci USA 103:4819-4824.
Hang HC, Yu C, Kato DL, Bertozzi CR, A metabolic labeling approach toward proteomic analysis of mucin-type O-linked glycosylation, (2003) Proc Natl Acad Sci USA 100:14846-14851.
Becker, D. J. & Lowe, J. B., Fucose: biosynthesis and biological function in mammals, (2003) Glycobiology 13, 41R-53R.
Keppler OT, Horstkorte R, Pawlita M, Schmidt C, Reutter W, Fucose: biosynthesis and biological function in mammals, (2001) Glycobiology 11:11R-18R.

(Continued)

Primary Examiner — Jacob Cheu
(74) Attorney, Agent, or Firm — Eckman Basu LLP; Shantanu Basu

(57) ABSTRACT

The present disclosure relates to a method for metabolic oligosaccharide engineering that incorporates derivatized alkyne-bearing sugar analogs as "tags" into cellular glycoconjugates. The disclosed method incorporates alkynyl derivatized Fuc and alkynyl derivatized ManNAc sugars into a cellular glycoconjugate. A chemical probe comprising an azide group and a visual probe or a fluorogenic probe is used to label the alkyne-derivatized sugar-tagged glycoconjugate. In one aspect, the chemical probe binds covalently to the alkynyl group by Cu(I)-catalyzed [3+2] azide-alkyne cycloaddition and is visualized at the cell surface, intracellularly, or in a cellular extract. The labeled glycoconjugate is capable of detection by flow cytometry, SDS-PAGE, Western blot, ELISA or confocal microscopy, and mass spectrometry.

64 Claims, 16 Drawing Sheets

OTHER PUBLICATIONS

Rostovtsev VV, Green LG, Fokin VV, Sharpless KB, A Stepwise Huisgen Cycloaddition Process: Copper(I)-Catalyzed Regioselective "Ligation" of Azides and Terminal Alkynes**, (2002) Angew Chem Int Ed Engl 41:2596-2599.

Wang Q, Chan TR, Hilgraf R, Fokin VV, Sharpless KB, Finn MG, Bioconjugation by Copper(I)-Catalyzed Azide-Alkyne [3 + 2] Cycloaddition, (2003) J Am Chem Soc 125:3192-3193.

Jacobs CL, Yarema KJ, Mahal LK, Nauman DA, Charters NW, Bertozzi CR, Metabolic Labeling of Glycoproteins with Chemical Tags through Unnatural Sialic Acid Biosynthesis, (2000) Methods Enzymol 327:260-275.

Sarkar AK, Fritz TA, Taylor WH, Esko JD, Disaccharide uptake and priming in animal cells: Inhibition of sialyl Lewis Xby acetylated GalIII1-4GlcNAc13-Onaphthalenemethanol, (1995) Proc Natl Acad Sci USA 92:3323-3327.

Sivakumar K, Xie F, Cash BM, Long S, Barnhill HN, Wang Q, A Fluorogenic 1,3-Dipolar Cycloaddition Reaction of 3-Azidocoumarins and Acetylenes, (2004) Org Lett 6:4603-4606.

Yarema KJ, Mahal LK, Bruehl RE, Rodriguez EC, Bertozzi CR, Metabolic Delivery of Ketone Groups to Sialic Acid Residues, (1998) J Biol Chem 273:31168-31179.

Speers AE, Cravatt BF, Profiling Enzyme Activities In Vivo Using Click Chemistry Methods, (2004) Chem Biol 11:535-546.

Hanson S, Best M, Bryan MC, Wong CH, Chemoenzymatic synthesis of oligosaccharides and glycoproteins (2004) Trends Biochem Sci 29:656-663.

Luchansky SJ, Bertozzi CR, Azido Sialic Acids Can Modulate Cell-Surface Interactions, (2004) Chembiochem 5:1706-1709.

Fujihashi M, Peapus DH, Kamiya N, Nagata Y, Miki K, Crystal Structure of Fucose-Specific Lectin from *Aleuria aurantia* Binding Ligands at Three of Its Five Sugar Recognition Sites, (2003) Biochemistry 42:11093-11099.

Wimmerova M, Mitchell E, Sanchez JF, Gautier C, Imberty A, Crystal Structure of Fungal Lectin, (2003) J Biol Chem 278:27059-27067.

Simanek EE, McGarvey GJ, Jablonowski JA, Wong CH, Selectin-Carbohydrate Interactions: From Natural Ligands to Designed Mimics, (1998) Chem Rev 98:833-862.

Yang L, McRae R, Henary MM, Patel R, Lai B, Vogt S, Fahrni CJ, Imaging of the intracellular topography of copper with a fluorescent sensor and by synchrotron x-ray fluorescence microscopy, (2005) Proc Natl Acad Sci USA 102:11179-11184.

Apweiler, R., Hermjakob, H. & Sharon, N., On the frequency of protein glycosylation, as deduced from analysis of the SWISS-PROT database, (1999) Biochim. Biophys. Acta 1473, 4-8.

Staudacher, E., α 1,3-Fucosyltransferases, (1996) Trends Glycosci. Glycotechnol. 8, 391-408.

Sears, P. & Wong, C.-H., Enzyme action in glycoprotein synthesis, (1998) Cell. Mol. Life Sci. 54, 223-252.

Haltiwanger, R. S. & Lowe, J. B., Role of glycosylation in development, (2004) Annu. Rev. Biochem. 73, 491-537.

Hirabayashi, J., Lectin-based structural glycomics: Glycoproteomics and glycan profiling, (2004) Glycoconj. J. 21, 35-40.

Shriver, Z., Raguram, S. & Sasisekharan, R., Glycomics: a pathway to a class of new and improved therapeutics, (2004) Nat. Rev. Drug Discov. 3, 863-873.

Khidekel, N., Ficarro, S. B., Peters, E. C. & Hsieh-Wilson, L. C., Exploring the O-GlcNAc proteome: Direct identification of O-GlcNAc-modified proteins from the brain, (2004) Proc. Natl. Acad. Sci. USA 101, 13132-13137.

Ratner, D. M., Adams, E. W., Disney, M. D. & Seeberger, P. H., Tools for Glycomics: Mapping Interactions of Carbohydrates in Biological Systems, (2004) ChemBioChem 5, 1375-1383.

Prescher, J. A. & Bertozzi, C. R., Chemistry in living systems, (2005) Nat. Chem. Biol. 1, 13-21.

Raman, R., Raguram, S., Venkataraman, G., Paulson, J. C. & Sasisekharan, R., Glycomics: an integrated systems approach to structure-function relationships of glycans, (2005) Nat. Methods 2, 817-824.

Chudakov, D. M., Lukyanov, S. & Lukyanov, K. A., Fluorescent proteins as a toolkit for in vivo imaging, (2005) Trends Biotechnol. 23, 605-613.

Kolb, H. C. & Sharpless, K. B., The growing impact of click chemistry on drug discovery, (2003) Drug Discov. Today 8, 1128-1137.

Zhou, Z. & Fahrni, C. J., A Fluorogenic Probe for the Copper(I)-Catalyzed Azide-Alkyne Ligation Reaction: Modulation of the Fluorescence Emission via 3 (n,δ*)-1(δ,δ*) Inversion, (2004) J. Am. Chem. Soc. 126, 8862-8863.

de Silva, A. P., Gunaratne, H. Q. N. & Gunnlaugsson, T., Flourescent PET(Photoinduced Electron Transfer) Reagents for Thiols, (1998) Tetrahedron Lett. 39, 5077-5080.

McAdam, C. J., Morgan, J. L., Murray, R. E., Robinson, B. H. & Simpson, J., Synthesis and Flourescence Properties of New Enaminenaphthalimides, (2004) Aust. J. Chem. 57, 525-530.

Tonetti, M., Sturla, L., Bisso, A., Zanardi, D., Benatti, U. & De Flora, A., The metabolism of 6-deoxyhexoses in bacterial and animal cells, (1998) Biochimie 80, 923-931.

Zeitler, R., Danneschewski, S., Lindhorst, T., Thiem, J. & Reutter, W., Inhibition of L-fucokinase from rat liver by L-fucose analogues in vitro, (1997) J. Enzyme lnhib. 11, 265-273.

Yurcheno, P. D. & Atkinson, P. H., Fucosyl-Glycoprotein and Precursor Pools in HeLa Cells, (1975) Biochemistry 14, 3107-3114.

Yurcheno, P. D. & Atkinson, P. H., Equilibration of Fucosyl Glycoprotein Pools in HeLa Cells, (1977) Biochemistry 14, 944-953.

Dube, D. H. & Bertozzi, C. R., Metabolic oligosaccharide engineering as a tool for glycobiology, (2003) Curr. Opin. Chem. Biol. 7, 616-625.

Düffels, A., Green, L. G., Lenz, R., Ley, S. V., Vincent, S. P. & Wong, C.-H., Chemoenzymatic Synthesis of L-Galactosylated Dimeric Sialyl Lewis X Structures Employing -1,3-Fucosyltransferase V, (2000) Bioorg. Med. Chem. 8, 2519-2525.

Srivastava, G., Kaur, K. J., Hindsgaul, O. & Palcic, M. M., Enzymatic Transfer of a Preassembled Trisaccharide Antigen to Cell Surfaces Using a Fucosyltransferase, (1992) J. Biol. Chem. 267, 22356-22361.

Vogel, C., Bergemann, C., Ott, A.-J., Lindhorst, T. K., Thiem, J., Dahlhoff, W. V., Hägren C., Palcic, M. M. & Hindsgaul, O., Synthesis of Carbon-Backbone-Elongated GDP-L-Fucose Derivatives as Substartes for Fucosyltransferase-Catalysed Reactions, (1997) Liebigs Ann. 601-612.

Binch, H., Stangier, K. & Thiem, J., Chemical synthesis of GDP-L-galactose and analogues, (1998) Carbohydr. Res. 306, 409-419.

Gilbert, J. C. & Weerasooriya, U., Diazoethenes: their attempted synthesis from akehydes and aromatic ketones by way of the Horner-Emmons modification of the Wittig reaction. A facile synthesis of Alkynes1-3, (1982) J. Org. Chem. 47, 1837-1845.

Huisgen, R., 1,3-Dipolar Cycloadditions Past and Future, (1963) Angew. Chem. Int. Ed. Engl. 2, 565-632.

Chan, T. R., Hilgraf, R., Sharpless, K. B. & Fokin, V. V., Polytriazoles as Copper(I)-Stabilizing Ligands in Catalysis, (2004) Org. Lett. 6, 2853-2855.

Lewis, W. G., Magallon, F. G., Fokin, V. V. & Finn, M. G., Discovery and Characterization of Catalysts for Azide-Alkyne Cycloaddition by Fluorescence Quenching, (2004) J. Am. Chem. Soc. 126, 9152-9153.

Wittmann, V. & Wong, C.-H., 1H-Tetrazole as Catalyst in Phosphomorpholidate Coupling Reactions: Efficient Synthesis of GDP-Fucose, GDP-Mannose, and UDP-Galactose, (1997) J. Org. Chem. 62, 2144-2147.

Fazio, F., Bryan, M. C., Blixt, O., Paulson, J. C. & Wong, C.-H., Synthesis of Sugar Arrays in Microtiter Plate, (2002) J. Am. Chem. Soc. 124, 14397-14402.

Bryan, M. C., Lee, L. V. & Wong, C.-H., High-throughput identification of fucosyltransferase inhibitors using carbohydrate microarrays, (2004) Bioorg. Med. Chem. Lett. 14, 3185-3188.

Ryde 'n, I., Påhlsson, P. & Lindgren, S., Diagnostic Accuracy of α1-Acid Glycoprotein Fucosylation for Liver Cirrhosis in Patients Undergoing Hepatic Biopsy, (2002) Clin. Chem. 48, 2195-2201.

Hashimoto, S., Asao, T., Takahashi, J., Yagihashi, Y., Nishimura, T., Saniabadi, A. R., Poland, D. C., van Dijk, W., Kuwano, H., Kochibe, N. & Yazawa, S., α1-Acid Glycoprotein Fucosylation as a Marker of Carcinoma Progression and Prognosis, (2004) Cancer 101, 2825-2836.

Link, A. J. Vink, M. K. S. & Tirrell, D. A., Presentation and Detection of Azide Functionality in Bacterial Cell Surface Proteins, (2004) J. Am. Chem. Soc. 126, 10598-10602.

Walz, G., Aruffo, A., Kolanus, W., Bevilacqua, M. & Seed, B., Recognition by ELAM-1 of the Sialyl-Lex Determinant on Myeloid and Tumor Cells, (1990) Science 250, 1132-1135.

Taniguchi, N., Ekuni, A., Ko, J. H., Miyoshi, E., Ikeda, Y., lhara, Y., Nishikawa, A., Honke, K. & Takahashi, M., A glycomic approach to the identification and characterization of glycoprotein function in cells transfected with glycosyltransferase genes, (2001) Proteomics 1, 239-247.

Kannagi, R., Izawa, M., Koike, T., Miyazaki, K. & Kimura, N., Carbohydrate-mediated cell adhesion in cancer metastasis and angiogenesis, (2004) Cancer Sci. 95, 377-384.

Miyoshi, E., Noda, K., Yamaguchi, Y., Inoue, S., Ikeda, Y., Wang, W., Ko, J. H., Uozumi, N., Li, W. & Taniguchi, N., The a1-6-fucosyltransferase gene and its biological significance, (1999) Biochim. Biophys. Acta 1473, 9-20.

Hakomori, S. & Zhang, Y., Glycosphingolipid antigens and cancer therapy, (1997) Chem. Biol. 4, 97-104.

Kannagi, R., Levery, S. B., Ishigami, F., Hakomori, S. I., Shevinsky, L. H., Knowles, B. B. & Solter, D., New Globoseries Glycosphingolipids in Human Teratocarcinoma Reactive with the Monoclonal Antibody Directed to a Developmentally Regulated Antigen, Stage-specific Embryonic Antigen 3, (1983) J. Biol. Chem. 258, 8934-8942.

Huang, C.-Y., Thayer, D. A., Chang, A. Y., Best, M. D., Hoffmann, J., Head, S. & Wong, C.-H., Carbohydrate microarray for profiling the antibodies interacting with Globo H tumor antigen, (2006) Proc. Natl. Acad. Sci. USA 103, 15-20.

Schottelius, A. J., Hamann, A. & Asadullah, K., Role of fucosyltransferases in leukocyte trafficking: major impact for cutaneous immunity, (2003) Trends Immunol. 24, 101-104.

Javaud, C., Dupuy, F., Maftah, A., Julien, R. & Petit, J. M., The fucosyltransferase gene family: an amazing summary of the underlying mechanisms of gene evolution, (2003) Genetica 118, 157-170.

Roos, C., Kolmer, M., Mattila, P. & Renkonen, R., Composition of *Drosophila melanogaster* Proteome Involved in Fucosylated Glycan Metabolism, (2002) J. Biol. Chem. 277, 3168-3175.

Baboval, T. & Smith, F. I., Compatison of human and mouse Fuc-TX and Fuc-TXI genes, and expression studies in the mouse, (2002) Mamm. Genome 13, 538-541.

Oriol, R., Mollicone, R., Cailleau, A., Balanzino, L. & Breton, C., Divergent evolution of fucosyltransferase genes from vertebrates, invertebrates, and bacteria, (1999) Glycobiology 9, 323-334.

Staudacher, E., Altmann, F., Wilson, I. B. H. & März, L., Fucose in N-glycans: from plant to man, (1999) Biochim. Biophys. Acta 1473, 216-236.

Piller, V., Piller, F. & Fukuda, M., Biosynthesis of Truncated O-Glycans in the T Cell Line Jurkat, (1990) J. Biol. Chem. 265, 9264-9271.

Mitchell, M. L., Tian, F., Lee, L. V. & Wong, C.-H., Synthesis and Evaluation of Transition-State Analogue Ingibitors of a-1,3-Fucosyltransferase, (2002), Angew. Chem. Int. Ed. Engl. 41, 3041-3044.

Lee, L. V., Mitchell, M. L., Huang, S.-J., Fokin, V. V., Sharpless, K. B. & Wong, C.-H., A Potent and Highly Selective Inhibitor of Human r-1,3-Fucosyltransferase via Click Chemistry, (2003) J. Am. Chem. Soc. 125, 9588-9589.

Hanson S. R., Hsu T. L., Weerapana E., Kishikawa K., Simon G. M., Cravatt B. F., Wong C. H., Tailored glycoproteomics and glycan site mapping using saccharide-selective bioorthogonal probes (2007) J Am Chem Soc. 129, 7266-7267.

Lowe, JB; Marth, JD., A Genetic Approach to Mammalian Glycan Funciton, Annu Rev Biochem. 2003;72:643-91.

Sears, P; Wong, CH. Toward Automated Synthesis of Oligosaccharides and Glycoproteins,Science. 2001;291:2344-50.

Grogan, MJ; Hanson, S; Best, M; Bryan, MC; Wong, CH., Chemoenzymatic synthesis of oligosaccharides and glycoproteins, Trend Biochem Sci. 2004;29:656-63.

Brik, A; Ficht, S; Wong, CH. Strategies for the preparation of homogenous glycoproteins, Cur Opin Chem Biol. 2006;10:638-44.

Bond, MR; Kohler, JJ. Chemical methods for glycoprotein discovery, Curr Opin Chem Biol. 2007;11:52-8.

Morelle, W; Canis, K; Chirat, F; Faid, V; Michalski, JC. The use of mass spectrometry for the proteomic analysis of glycosylation, Proteomics. 2006;6:3993-4015.

Prescher, JA; Bertozzi, CR. Chemical Technologies for Probing Glycans, Cell. 2006;126:851-854.

Laughlin, ST; Agard, NJ; Baskin, JM; Carrico, IS; Chang, PV; Ganguli, AS; Hangauer, MJ; Lo, A; Prescher, JA; Bertozzi, CR; Minoru, F., Metabolic Labeling of Glycans with Azido Sugars for Visualization and Glycoproteometics, Meth Enzym. vol. 415. Academic Press; 2006. pp. 230-250.

Speers, AE; Cravatt, BF., A Tandem Orthogonal Proteolysis Strategy for High-Content Chemical Proteomics, J Am Chem Soc. 2005;127:10018-9.

Zhang, H; Li, XJ; Martin, DB; Aebersold, R., A Tandem Orthogonal Proteolysis Strategy for High-Content Chemical Proteomics, Nat Biotech. 2003;21:660-6.

Kaji, H; Saito, H;Yamauchi, Y; Shinkawa, T; Taoka, M; Hirabayashi, J; Kasai, K; Takahashi, N; Isobe, T., A Tandem Orthogonal Proteolysis Strategy for High-Content Chemical Proteomics, Nat Biotech. 2003;21:667-72.

Kaji, H; Isobe, T., Large-Scale Analysis of Glycoproteins by LC-MS Method, Trend Glycosci Glycotech. 2006;18:313-22.

Eng, JK; McCormack, AL; Yates, JR., An approach to correlate tandem mass spectral data of peptides with amino acid sequences in a protein database, J Amer Soc Mass Spec. 1994;5:976-89.

Washburn, MP; Wolters, D; Yates, JR., Large-scale analysis of the yeast proteome by multidimensional protein identification technology, 3rd Nat Biotech. 2001;19:242-7.

Swiss-Prot database (www.expasy.org), 1999.

Lewandrowski, U; Moebius, J; Walter, U; Sickmann, A., Elucidation of N-Glycosylation Sites on Human Platelet Proteins, Mol Cell Proteomics. 2006;5:226.

Ramachandran, P; Boontheung, P; Xie, YM; Sondej, M; Wong, DT; Loo, JA., Identification of N-Linked Glycoproteins in Human Saliva by Glycoprotein Capture and Mass Spectrometry, J Proteome Res. 2006;5:1493.

Liu, T; Qian, WJ; Gritsenko, MA; Campli, DG; Monroe, ME; Moore, RJ; Smith, RD., Human Plasma N-Glycoproteome Analysis by Immunoaffinity Subtraction, Hydrazide Chemistry, and Mass Spectrometry, J Prot Res. 2005;4:2070.

Roth, J., Protein N-Glycosylation along the Secretory Pathway: Relationship to Organelle Topography and Function, Protein Quality Control, and Cell Interactions, Chem Rev. 2002;102:285-304.

Shiraki, K; Takase, K; Tameda, Y; Hamada, M; Kosaka, Y; Nakano, T., A clinical study of lectin-reactive alpha-fetoprotein as an early indicator of hepatocellular carcinoma in the follow-upof cirrhotic patients, Hepatology. 1995;22:802-7.

Comunale, MA; Lowman, M; Long, RE; Krakover, J; Philip, R; Seeholzer, S; Evans, AA; Hann, HWL; Block, TM; Mehta, AS., Proteomic analysis of serum associated fucosylated glycoproteins in the development of primary hepatocellular carcinoma, J Proteome Res. 2006;5:3108-15.

Wells, L; Vosseller, K; Cole, RN; Cronshaw, JM; Matunis, MJ; Hart, GW., Mapping Sites of O-GlcNAc Modification Using Affinity Tags for Serine and Threonine Post-translational Modifications, Mol Cell Proteomics. 2002;1:791-804.

Vosseller, K; Trinidad, JC; Chalkley, RJ; Specht, CG; Thalhammer, A; Lynn, AJ; Snedecor, JO; Guan, S; Medzihradszky, KF; Maltby, DA; Schoepfer, R; Burlingame, AL., O-Linked N-Acetylglucosamine Proteomics of Postsynaptic Density Preparations Using Lectin Weak Affinity Chromatography and Mass Spectrometry, Mol Cell Proteomics. 2006;5:923-34.

* cited by examiner

| No. | Name | Associated disease |
|-----|------|--------------------|
| 1 | EF-Tu | Gastric cancer |
| 2 | Catalase | Gastric cancer |
| 3 | Heat shock protein 60 | Gastric cancer/Duodenal ulcer |
| 4 | FTSH (cell division protease) | Gastric cancer |
| 5 | DNAK (HSP 70) | Gastric cancer |
| 6 | CLPB (chaperone) | Gastric cancer |
| 7 | CAGA (immuniodominant antigen) | Gastric cancer |
| 8 | ATPase-alpha subunit | Gastric ulcer |
| 9 | UreB | Gastric ulcer |

…

ALKYNYL SUGAR ANALOGS FOR THE LABELING AND VISUALIZATION OF GLYCOCONJUGATES IN CELLS

RELATED APPLICATIONS

This application claims priority to U.S. Provisional Patent Application Ser. No. 60/896,777, filed on Mar. 23, 2007, titled "Pro-alkynyl sugar analogs for the labeling and visualization of glycoconjugates in cells", the entirety of this application hereby incorporated by reference.

GOVERNMENT SUPPORT

This disclosure was supported, in whole or in part, by the National Institutes of Health and the Skaggs Institute for Chemical Biology.

FIELD OF THE DISCLOSURE

The present disclosure provides a method for metabolic oligosaccharide engineering which uses azido and/or alkyne-bearing sugar analogs and/or precursors of fucose and sialic acid to incorporate azido and/or alkyne tags into cellular glycans that are fucosylated and sialylated. The derivatized glycan is labeled by a chemical probe comprising an azide group and a visualizable, isolatable, and/or fluorogenic group. The chemical probe binds covalently (labels) to the alkynyl and/or azido groups displayed in cellular glycans via the copper (I)-catalyzed [3+2] azide-alkyne cycloaddition (CuAAC) or azide-a. The labeled glycans can be visualized at the cell surface, intracellularly, or in a cellular extract.

BACKGROUND

Glycans are integral components of biological systems with far reaching activities, many of which are only beginning to be understood. Glycans constitute the most abundant and diverse class of biomolecules found in natural systems, consisting of oligosaccharide chains that are present as independent polysaccharides (e.g., cellulose, an important structural component in plants; and heparin sulfate, an import factor of blood clotting in mammals) or as glycoconjugates with lipids (glycolipids), proteins (glycoproteins, proteoglycans), and small molecule natural products (e.g., antibiotics such as erythromycin, vancomycin, and teicoplanin).

Glycans play a role in almost every aspect of cellular activity. Most glycans in higher eukaryotes are produced in the secretory pathway by glycosylation events, which entail the enzymatic transfer of saccharides or oligosaccharide chains onto lipids and proteins. Protein glycosylation is a complex co- or post-translational process that modifies the majority of the human proteome and serves a vast array of biological functions. Protein glycosylation exerts intrinsic effects on structure, from mediating folding and oligimerization, to increasing stability, solubility, and circulation time. Inside of the cell, glycans affect recognition, binding, targeting, and cellular distribution. At the cell surface, glycans are prominently displayed where they are involved in a host of molecular recognition events that modulate important physiological processes, such as cell-cell adhesion, inflammation, angiogenesis, coagulation, embryogenesis, differentiation, communication, and a myriad of other cellular signaling pathways.

Cell surface glycans have also been associated with physiological dysfunctions such as bacterial and viral infection, rheumatoid arthritis, and tumor progression. In the latter case, several types of oncofetal and aberrant glycans have been established to correlate with malignancy, invasiveness, inflammation and cancer metastasis. In particular, altered terminal fucosylation and sialylation, which are believed to result from changes in expression locations and levels of fucosyltransferases (an group of enzymes that transfers a fucose from a donor substrate to an acceptor substrate, a glycoconjugate or glycan) and sialyltransferases (a group of enzymes that transfers a sialic acid from a donor substrate to an acceptor substrate, a glycoconjugate or glycan) respectively, are associated with tumor malignancy. For example, glycan determinants like Lewis y, Lewis x, sialyl Lewis x, sialyl Lewis a, sialyl Tn, Globo H, fucosyl GM1, and polysialic acid are expressed at elevated levels in neoplastic tissues. For this reason, these epitopes are promising and eagerly pursued targets for glycan-based vaccines. Additionally, several congenital glycosylation disorders, lysosomal storage disorders, and immunological diseases have been linked with dysregulation of glycan catabolism/metabolism. Although known to be involved in physiological and pathophysiological events, the identification of many glycan structures and delineation of their mode of action at the molecular level has been complicated by their underpinning complexity.

Glycan complexity results from many factors. They are synthesized in a non-templated, post-translational process, which means that sites of glycoconjugate glycosylation and structures within them have proven, thus far, to be minimally predictable. This also means that glycans cannot be genetically manipulated in a similar fashion to DNA and proteins. Glycans are synthesized in the secretory pathway by a suite of enzymes that are subject to multifaceted controls. The end glycan products can have enormous structural complexity (many possible glycan structures, the diversity of which is also a function of the sugar building blocks), structural microheterogeneity (multiple different glycan structures attached to a glycoconjugate at the same position), and structural macro-heterogeneity (multiple sites and types of glycan attachment; for example, glycoproteins can be N-linked at Asn residues, or O-linked at Ser/Thr residues). Heterogeneity in glycan structures appears to be dynamically regulated and functionally significant, governing multivalent interactions on the cell surface. Heterogeneity and multivalency complicate structure-function studies and the isolation of homogenous glycans in meaningful amounts from natural sources is nearly impossible. For the procurement of homogenous glycoconjugates/glycans synthesis is the only viable route, but remains one of the most formidable challenges in glycobiology.

The link between glycan activity and complexity has presented major challenges to deciphering their activities on an individual protein, let alone, proteomic scale. Among the challenges facing global analysis are development of general methods for isolating glycans from complex proteomes; determining saccharide composition, site of protein modification, and fraction occupancy; and understanding the direct roles of glycans in cellular function and dysfunction.

Specific glycan-tagging systems provide a powerful method for probing the structure of heterogeneous glycans. The key to glycan tagging entails incorporating modified sugars derivatized with chemical reporting groups into cellular glycans (typically via the normal biosynthetic pathways, a process known as metabolic oligosaccharide engineering, or MOE) and then detecting the tagged-glycans by labeling their chemical reporting groups with a complementary probe that chemically reacts with them in a specific manner (a chemoselective manner). Many selective chemical probing techniques have been used for probing chemical reporting group-tagged glycoconjugates in cells. These methods include bioorthogonal reactions such as ketoneaminooxy/hydrazide ligation, Staudinger ligation, Michael addition, and the strain-promoted, and Cu(I)-catalyzed [3+2] azide-alkyne cycloaddition (CuAAC). Several chemical reporting groups are tolerated and successfully incorporated into glycoconjugates using MOE, including ketones, thiols, photoreactive groups, azides, and alkynes. These reporting sugars have been labeled with tags such as FLAG peptides, biotin, and fluorescent or fluorogenic molecules. The strength of these systems is that the labeled glycan products have the potential to be manipulated for specific glycan studies involving: enrichment and glycoproteomic analysis by means of mass spectrometry detection and/or quantitation by flow cytometry or visualization through microscopy to obtain information about glycan localization, trafficking, and dynamics.

The incorporation of exogenous natural or unnatural sugars into glycans has been achieved by cellular biosynthetic pathways. These processes involve multistep enzymatic transformations that render free sugars in the cytosol into nucleotide-donor sugars, the substrates for glycosyltransferases. In the case of fucose (Fuc), a salvage pathway consisting of Fuc kinase and GDP-Fuc (guanosine diphosphate fucose) pyrophosphorylase contributes to the production of GDP-Fuc, which is then exploited by fucosyltransferases (FucTs) located in the Golgi apparatus to add Fuc onto glycoconjugates. Modifications at the 6-position of Fuc are tolerated by the salvage pathway and FucTs. In the sialic acid (NeuAc) biosynthetic pathway, the precursor N-acetylmannosamine (ManNAc) is derived from GlcNAc or UDP-GlcNAc through specific epimerases, then sequentially converted to sialic acid (NeuAc) by the cytosolic enzymes ManNAc 6-kinase, sialic acid-9-phosphate synthase, and sialic acid-9-phosphate phosphatase. CMP-NeuAc is subsequently formed in the nucleus, and transported to the Golgi apparatus for glycan elaboration by sialyltransferases. Studies on metabolic delivery of N-acetyl mannosamine or ManNAc analogs show that N-acyl chains up to five carbon atoms long are tolerated by the sialic acid biosynthetic pathway.

Prior glycoprotein probes have limited utility due to issues of cellular toxicity. The incorporation of exogenous natural or unnatural sugars comprising non-toxic probes into glycans by cellular biosynthetic pathways is important to study aberrant glycosylation. Further understanding of the molecular details and correlations between altered glycosylation and pathological status is of great interest and is likely to provide useful information for diagnosis and disease prognosis, in addition to unveiling new therapeutic targets.

Glycosylation is the process of glycoconjugate synthesis and is an important bioinformational process that occurs co- or posttranslationally on greater than 50% of eukaryotic proteins. In living organisms, it affects protein bioactivity and metabolic turnover. Inside of cells, it mediates protein folding, stability, and trafficking. At the cell surface, glycans participate in molecular recognition events that are central to biological and pathological processes like cell-cell interactions involved in adhesion, migration, and metastasis; host-pathogen interactions critical for bacterial and viral infections; and, initiation of immune response.

Aberrant glycosylation is often observed in pathological conditions such as inflammation and cancer metastasis. In particular, altered terminal fucosylation and sialylation, which are believed to result from changes in expression locations and levels of fucosyltransferases and sialyltransferases, are associated with tumor malignancy. For example, glycan determinants like Lewis y, Lewis x, sialyl Lewis x, sialyl Lewis a, sialyl Tn, Globo H, fucosyl GM1, and polysialic acid are expressed at elevated levels in neoplastic tissues. For this reason, these epitopes are promising and eagerly pursued targets for glycan-based vaccines. However, cellular glycans are complex, heterogeneous populations, resulting from a non-template-driven process that cannot be manipulated genetically. This complexity makes the isolation and identification of glycans for structural analysis one of the most challenging and defining tasks in glycobiology.

Specific glycan-tagging systems provide a powerful method for probing the structure of heterogeneous glycans. The key to glycoconjugate tagging entails incorporating derivatized sugar chemical reporting groups into cellular glycoconjugates (typically via the normal biosynthetic pathways, a process know as metabolic oligosaccharide engineering, or MOE), and then detecting the tagged glycoconjugates by labeling their chemical reporting groups with a complementary probe that chemically reacts with them in a specific manner. Many selective chemical probing techniques have been used for performing chemistry with chemical reporting group-tagged glycoconjugates in cells. These methods include bioorthogonal reactions such as ketoneaminooxy/hydrazide ligation, Staudinger ligation, Michael addition, and the strain-promoted and Cu(I)-catalyzed [3+2] azide-alkyne cycloaddition.

Several chemical reporting groups are tolerated and successfully incorporated into glycoconjugates using MOE, including ketones, thiols, photoreactive groups, azides, and alkynes. These reporting sugars have been labeled with tags, such as FLAG peptides, biotin, and fluorescent or fluorogenic molecules. The strength of these systems is that the labeled glycan products have the potential to be manipulated for specific glycan studies involving: enrichment and glycoproteomic analysis by mass spectrometry; detection and/or quantitation by flow cytometry; or visualization through microscopy to obtain information about glycan localization, trafficking, and dynamics.

The incorporation of exogenous natural or unnatural sugars into glycoconjugates is achieved by cellular biosynthetic pathways. These processes involve multistep enzymatic transformations that render free sugars in the cytosol into nucleotide-donor sugars, the substrates for glycosyltransferases. In the case of fucose (Fuc), a salvage pathway consisting of Fuc kinase and GDP-Fuc pyrophosphorylase contributes to the production of GDP-Fuc, which is then exploited by fucosyltransferases (FucTs) located in the Golgi apparatus to add Fuc onto glycoconjugates. Previous work has shown that modifications at the 6-position of Fuc are tolerated by the salvage pathway and FucTs. In the sialic acid (NeuAc) biosynthetic pathway, the precursor N-acetylmannosamine (ManNAc) is derived from N-acetylglucosamine (GlcNAc) or uridine diphosphate GlcNAc (UDP-GlcNAc) through specific epimerases, then sequentially converted to sialic acid by the cytosolic enzymes ManNAc 6-kinase, sialic acid-9-phosphate synthase, and sialic acid-9-phosphate phosphatase. Cytosine monophosphate NeuAc (CMP-NeuAc) is subsequently formed in the nucleus, and transported to the Golgi apparatus for glycan elaboration by sialyltransferases. Studies on metabolic delivery of ManNAc or its analogs show that N-acyl chains up to five carbon atoms long are tolerated by the sialic acid biosynthetic pathway.

Currently available glycoconjugate probes can be of limited utility due to potential cellular toxicity. The incorporation of exogenous natural or unnatural sugars comprising non-toxic probes into glycoconjugates by cellular biosynthetic pathways is important to study aberrant glycosylation which is often observed in pathological conditions such as inflammation and cancer metastasis. Further understanding of the molecular details and correlations between altered glycosylation and pathological status is of great interest and is likely to provide useful information for diagnosis and disease prognosis, in addition to unveiling new therapeutic targets.

SUMMARY OF THE INVENTION

In one exemplary implementation, a method is disclosed comprising presenting an alkynyl-derivatized sugar to a cell, wherein the alkynyl-derivatized sugar has an alkynyl functional group, and wherein the cell is capable of producing a glycoconjugate; incorporating the alkynyl-derivatized sugar into the cell, wherein the alkynyl-derivatized sugar is subsequently used by the cell to produce a tagged glycoconjugate; wherein the tagged glycoconjugate includes:

a glycan portion; a conjugate portion; and an alkynyl functional group; and reacting the tagged glycoconjugate with a probe to produce a labeled, tagged glycoconjugate;

In another exemplary implementation, the labeled glycoconjugate is detected to determine the location of the labeled glycoconjugate in the cell.

In another exemplary implementation, the labeled glycoconjugate is detected to determine the quantity of the labeled glycoconjugate in the cell.

In another exemplary implementation, the labeled glycoconjugate is detected to determine the identity of the labeled glycoconjugate in the cell.

In another exemplary implementation, the alkynyl-derivatized sugar is an alkynyl-derivatized fucose.

In another exemplary implementation, the alkynyl-derivatized sugar is an alkynyl-derivatized fucose derivative.

In another exemplary implementation, the alkynyl-derivatized sugar is 1,2,3,4-tetraacetyl alkynyl fucose or a 1,2,3,4-tetraacetyl alkynyl fucose derivative.

In another exemplary implementation, the alkynyl-derivatized sugar is an alkynyl-derivatized N-acetylmannosine or an alkynyl-derivatized N-acetylmannosine derivative.

In another exemplary implementation, the alkynyl-derivatized sugar is a sialic acid precursor.

In another exemplary implementation, the alkynyl-derivatized sugar is 1,3,4,6-tetra-O-acetyl-N-4-pentynoylmannosamine.

In another exemplary implementation, the alkynyl-derivatized sugar is peracetylated.

In another exemplary implementation, the alkynyl-derivatized sugar is acetylated.

In another exemplary implementation, the alkynyl-derivatized sugar is ManNAcyne.

In another exemplary implementation, the alkynyl-derivatized sugar is NeuAcyne.

In another exemplary implementation, the alkynyl-derivatized sugar is Fucyne.

In another exemplary implementation, the alkynyl-derivatized sugar is bioorthogonal.

In another exemplary implementation, the alkynyl-derivatized sugar is subsequently incorporated into a glycoconjugate at a terminal position.

In another exemplary implementation, the alkynyl-derivatized sugar is subsequently incorporated into a glycoprotein.

In another exemplary implementation, the alkynyl-derivatized sugar is subsequently incorporated into a glycoprotein at a terminal position.

In another exemplary implementation, the alkynyl-derivatized sugar is subsequently incorporated into a glycolipid.

In another exemplary implementation, the alkynyl-derivatized sugar is subsequently incorporated into a glycolipid at a terminal position.

In another exemplary implementation, the alkynyl-derivatized sugar is capable of fluorescence.

In another exemplary implementation, the alkynyl-tagged glycoconjugate is a fucosylated glycoconjugate.

In another exemplary implementation, the alkynyl-tagged glycoconjugate is a sialylated glycoconjugate.

In another exemplary implementation, the probe is azido-derivatized.

In another exemplary implementation, the probe reacts with the alkynyl-tagged glycoconjugate by azide-alkyne cycloaddition.

In another exemplary implementation, the azide-alkyne cycloaddition reaction is copper (I) catalyzed.

In another exemplary implementation, the probe-tagged glycoconjugate reaction generates a triazole moiety.

In another exemplary implementation, the triazole moiety is generated while maintaining bioorthogonality of the functional groups.

In another exemplary implementation, the triazole moiety is generated at biological pH.

In another exemplary implementation, the triazole moiety is generated with nearly 100% reaction efficiency.

In another exemplary implementation, the probe is fluorogenic and becomes fluorescent upon azide-alkyne cycloaddition reaction with the tagged glycoconjugate.

In another exemplary implementation, the probe additionally comprises a biotin group.

In another exemplary implementation, the probe additionally comprises a coumarin group.

In another exemplary implementation, the coumarin probe is 3-azido-7-hydroxycoumarin.

In another exemplary implementation, the detecting step comprises visualizing the location of labeled glycoconjugates by one or more techniques of flow cytometry and confocal microscopy.

In another exemplary implementation, the detecting step comprises quantifying the labeled glycoconjugates by one or more techniques of flow cytometry, SDS-PAGE, Western blot, ELISA, confocal microscopy, and mass spectroscopy.

In another exemplary implementation, the detecting step comprises identifying the labeled glycoconjugates by one or more techniques of flow cytometry, SDS-PAGE, Western blot, ELISA and confocal microscopy.

In another exemplary implementation, the incorporating step further comprises growing the cell in the presence of from about 1 to about 1000 micromolar concentration of the alkynyl-derivatized fucose.

In another exemplary implementation, the incorporating step comprises growing the cell in the presence of from about 50 to about 400 micromolar concentration of the alkynyl-derivatized fucose.

In another exemplary implementation, the incorporating step comprises growing the cell in the presence of from about 1 to about 100 micromolar concentration of the alkynyl-derivatized N-acetylmannosamine.

In another exemplary implementation, the incorporating step comprises growing the cell in the presence of from about 5 to about 50 micromolar concentration of the alkynyl-derivatized N-acetylmannosamine.

In another exemplary implementation, the labeled glycoconjugate in the cell is on the surface of the cell.

In another exemplary implementation, the cells are permeabilized prior to labeling.

In another exemplary implementation, a method is disclosed comprising presenting an alkynyl-derivatized sugar to a cell, wherein the alkynyl-derivatized sugar has an alkynyl functional group, and wherein the cell is capable of producing a glycoconjugate; incorporating the alkynyl-derivatized sugar into the cell, wherein the alkynyl-derivatized sugar is subsequently used by the cell to produce a tagged glycoconjugate;

wherein the tagged glycoconjugate includes a glycan portion; a conjugate portion; and an alkynyl functional group; and reacting the tagged glycoconjugate with a probe to produce a labeled, tagged glycoconjugate; wherein the resultant toxicity of the method is improved by at least 10% as compared to presenting an azido-derivatized sugar to produce the tagged glycoconjugate.

In another exemplary implementation, the resultant toxicity is improved by at least 50%.

In another exemplary implementation, a compound is disclosed comprising: an alkynyl tagged glycoconjugate; and an azido-derivatized probe;

wherein the alkynyl tagged glycoconjugate and azido-derivatized probe are joined via a triazole moiety.

In another exemplary implementation, the compound is fluorogenic.

In another exemplary implementation, the resultant toxicity measured when the compound is presented to a cell or cells is increased by no more than 10% as compared to the toxicity measured in a cell or cells to which no compound is presented.

In another exemplary implementation, the azido-derivatized probe further comprises a biotin-labeled moiety.

In another exemplary implementation, the azido-derivatized probe further comprises an antibody-labeled moiety.

In another exemplary implementation, an alkynyl-derivatized fucose is formed by the process of: obtaining 1-(+)-galactonic acid γ-lactone; transforming, 1-(+)-galactonic acid γ-lactone to 1,2:3,4-Di-O-isopropylidene-☐-L-galactose by treatment with Amberlite IR120 and NaBH$_4$; transforming the hydroxyl group at position 6 of 1,2:3,4-Di-O-isopropylidene-☐-L-galactose to an alkynyl group by Seyferth-Gilbert homologation, or specifically first by treatment with PCC and NaOAc; filtering this mixture through a bed of silica gel, and then treating the filtrate with a suspension of tBuOK and (EtO)$_2$P(O)CHN$_2$, thus creating 6,7-deoxy-1,2:3,4-di-O-isopropylidene-☐-L-galacto-hept-6-ynopyranoside, referred to as 6-alkynylfucose diacetonide, or the diisopropylidene-Fuc intermediate; removing the diacetonide protecting groups from 6-alkynylfucose diacetonide to form 6-alkynyl fucose; and acetylating the resultant deprotected product 6-alkynyl fucose to form 1,2,3,4-tetraacetyl alkynyl fucose, as a mixture of pyranoside and furanoside forms;

In another exemplary implementation, an azido-derivatized fucose is prepared by the process of: obtaining 1-(+)-galactonic acid γ-lactone; transforming 1-(+)-galactonic acid γ-lactone to 1,2:3,4-Di-O-isopropylidene-☐-L-galactose by treatment with Amberlite IR120 and NaBH$_4$; transforming the hydroxyl group at position 6 of 1,2:3,4-Di-O-isopropylidene-☐-L-galactose to an azido group by treatment with TsCl and NaN$_3$ to create 6,7-deoxy-1,2:3,4-di-O-isopropylidene-☐-L-Fucose-6-azide, referred to as 6-azidofucose diacetonide, or the diisopropylidene-Fuc intermediate; removing the diacetonide protecting groups from 6-alkynylfucose diacetonide to form 6-alkynyl fucose; and acetylating the resultant deprotected product 6-alkynyl fucose to form 1,2,3,4-tetraacetyl alkynyl fucose, as a mixture of pyranoside and furanoside forms.

In another exemplary implementation, an alkynyl-tagged glycoconjugate is made by the process of fucosylating a glycoconjugate with the 1,2,3,4-tetraacetyl alkynyl fucose by endogenous cellular metabolic pathways for glycan synthesis.

In another exemplary implementation, a compound is made by the steps of fucosylating a glycoconjugate with the 1,2,3,4-tetraacetyl alkynyl fucose by endogenous cellular metabolic pathways for glycan synthesis; and Coupling the azido-derivatized probe with the fucosylated glycoconjugate at least partially comprised of 1,2,3,4-tetraacetyl alkynyl fucose via cycloaddition.

In another exemplary implementation, an alkynyl ManNAc-tagged glycoconjugate is made by the process of: obtaining D-mannoside hydrochloride; reacting the D-mannoside hydrochloride with N-succinimidyl 4-pentynoate to yield alkynyl ManNAc derivative; acetylating the alkynyl ManNAc derivative; and sialylating a glycoconjugate with the acetylated alkynyl ManAc derivative.

In another exemplary implementation, a fluorescent glycoconjugate is made by the process of: obtaining D-mannoside hydrochloride; reacting the D-mannoside hydrochloride with N-succinimidyl 4-pentynoate to yield alkynyl ManNAc derivative; acetylating the alkynyl ManNAc derivative; sialylating a glycoconjugate with the acetylated alkynyl ManNAc derivative; and coupling an azido-derivatized probe with the sialylated glycoconjugate at least partially comprised of the acetylated alkynyl ManNAc derivative via cycloaddition.

In another exemplary implementation, A method is disclosed comprising the steps of: presenting an alkynyl-derivatized sugar to a cell, wherein the alkynyl-derivatized sugar has an alkynyl functional group, and wherein the cell is capable of producing a glycoconjugate; incorporating the alkynyl-derivatized sugar into the cell, wherein the alkynyl-derivatized sugar is subsequently used by the cell to produce a tagged glycoconjugate; wherein the tagged glycoconjugate includes a glycan portion; a conjugate portion; and an alkynyl functional group;

reacting the tagged glycoconjugate with a probe to produce a labeled, tagged glycoconjugate; detecting the labeled glycoconjugate; and differentially analyzing the proteomes of the cells incorporating detected, labeled glycoconjugate.

In another exemplary implementation, the cells are *H. pylori* or *H. pylori*-infected cells.

In another exemplary implementation, a method is disclosed comprising the steps of: providing an alkynyl-derivatized sugar to a cell population, wherein the alkynyl-derivatized sugar has an alkynyl functional group, and wherein the cells are capable of producing a glycoconjugate; incorporating the alkynyl-derivatized sugar into the cell, wherein the alkynyl-derivatized sugar is subsequently used by the cells to produce a tagged glycoconjugate.

wherein the tagged glycoconjugate includes a glycan portion; a conjugate portion; and an alkynyl functional group; reacting the tagged glycoconjugate with a probe to produce a labeled, tagged glycoconjugate; visualizing the labeled, tagged glycoconjugate population of the cells; and differentially analyzing the subset of cells expressing labeled, tagged Lewis antigen epitopes.

In another exemplary implementation, a method is disclosed comprising generating antibodies to the subset of cells expressing Lewis antigen epitopes.

In another exemplary implementation, cells are presented with derivatized sugars for a limited period of time.

In another exemplary implementation, the limited period of time is 30 minutes.

In another exemplary implementation, derivatized sugars are presented to a cell for a limited time, and the presenting step is succeeded by presenting the cell with non-derivatized sugars.

In another exemplary implementation, derivatized sugars are presented to a cell for a limited time, and both preceded and succeeded by presenting the cell with non-derivatized sugars.

In another exemplary implementation, derivatized sugars are subsequently labeled and detected at various time intervals subsequent to the limited presentment of such sugars to the cell.

In another exemplary implementation, various time interval detections of derivatized sugars are compared so as to assess cellular trafficking of glycoconjugates.

In another exemplary implementation, differential cellular trafficking of glycoconjugates is assessed.

In another exemplary implementation, various time interval detections of derivatized sugars are compared with various interval detections of the location of various intracellular and extracellular bodies (e.g. nucleus, Golgi apparatus, lysosome) so as to assess differential cellular trafficking of glycoconjugates.

In another exemplary implementation, derivatized sugars that are presented to a cell for a limited time are alkynyl-derivatized sugars.

In another exemplary implementation, derivatized sugars that are presented to a cell for a limited time are azido-derivatized sugars.

In another exemplary implementation, derivatized sugars that are presented to a cell for a limited time are both alkynyl and azido-derivatized sugars.

In another exemplary implementation, derivatized sugars that are presented to a cell for a limited time are incorporated into fucosylated glycoconjugates.

In another exemplary implementation, derivatized sugars that are presented to a cell for a limited time are incorporated into sialylated glycoconjugates.

In another exemplary implementation, derivatized sugars that are presented to a cell for a limited time and are preceded and succeeded by presenting the cell with non-derivatized sugars are incorporated into both fucosylated and sialylated glycoconjugates.

BRIEF DESCRIPTION OF THE FIGURES

The patent or application contains at least one drawing executed in color. Copies of this patent or patent application publication with color drawings will be provided by the Office upon request and payment of the necessary fee.

FIG. 1 (D) shows cell growth analysis after treatment with different derivatized sugar Fuc analogs: alkynyl Fuc 1, azido Fuc 2, control 3, and untreated. Jurkat cells were grown in the presence of 200 micromolar each Fuc analog for 3 days before cell numbers were counted. The data represent the percentage of treated cells vs. untreated cells (n=4).

FIG. 2 shows analysis of cell surface labeling of sialyl glycoconjugates.

DETAILED DESCRIPTION OF THE INVENTION

Figure 1A:
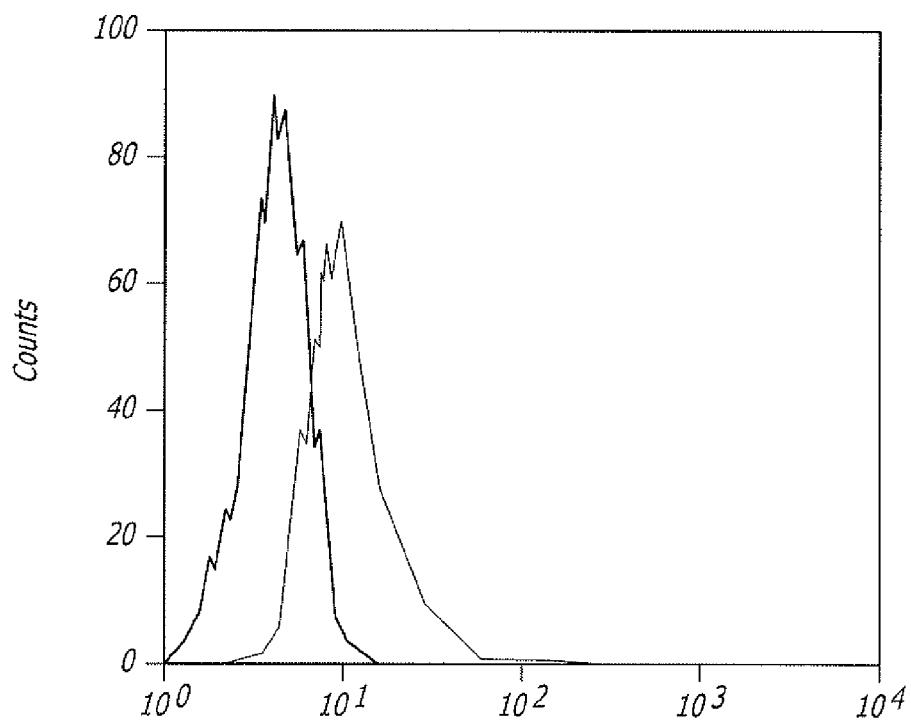
FIG. 1(A) shows flow cytometry analysis of Jurkat cells treated with Fuc alkynyl-derivatized analogs and labeled with biotin/fluorescein conjugated streptavidin (filled trace, untreated cells; black, cells treated with Fuc 3; grey, cells treated with alkynyl-derivatized Fuc 1).
Figure 1B:
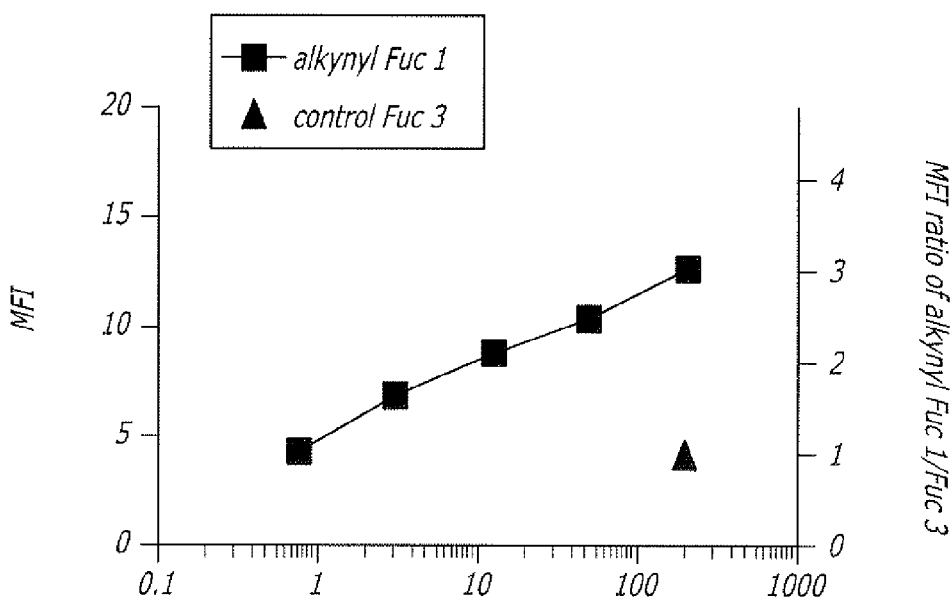
FIG. 1(B) shows dose-dependency of fucosyl-glycan tagging by alkynyl-derivatized Fuc 1 over 3 days.
Figure 1C:
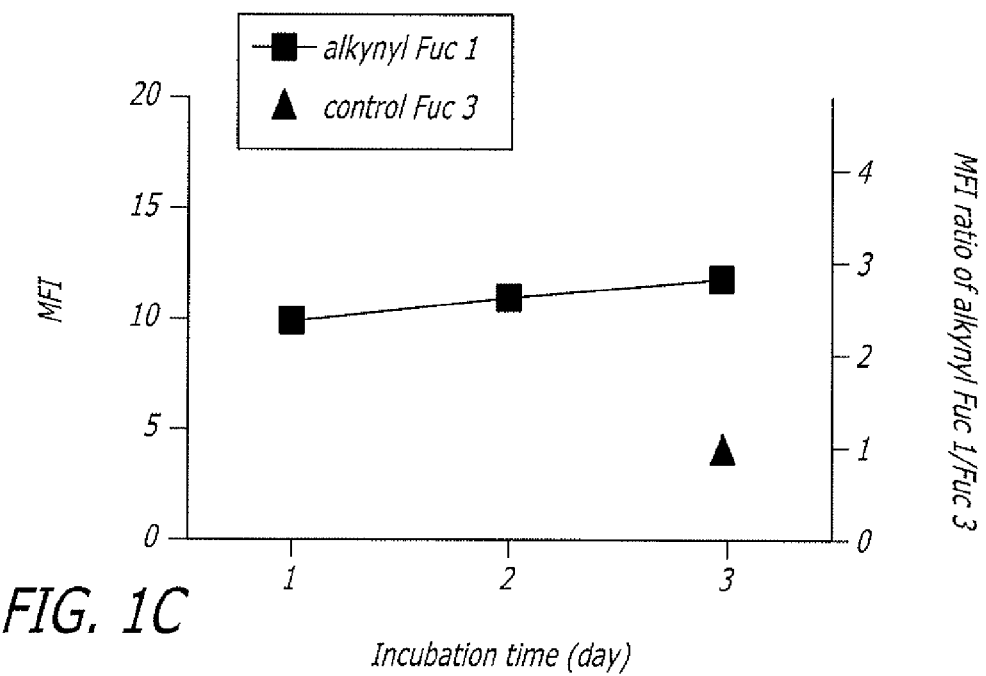
FIG. 1(C) shows the time course of fucosyl glycan tagging by 200 micromolar alkynyl Fuc 1.

As used herein, the term "abnormal" means an organism whose proteome differs in identity (whether measure by individual or total protein identity), relative ratio, and/or glycosylation status of measurable cellular proteins.

As used herein, the term "alkynyl group" or "alkyne functional group" means an alkyne functional group (also called acetylene functional group), which is a hydrocarbon comprised of a triple bond between two carbon atoms.

As used herein, the term "alkynyl-derivatized sugar" means a synthetic sugar analog, in pro-molecular, metabolic precursor, and/or downstream metabolite form, substituted with an alkynyl group.

As used herein, the term "alkynyl-derivatized" means a molecule in which at least one carbon is substituted with an alkynyl functional group.

As used herein, the term "alkynyl functional group" means a chemical moiety consisting of at least one triple bond between two carbon atoms, with the formula $C_nH_{2n-2}$.

As used herein, the term "alkynyl-tagged", means a glycoconjugate incorporating an alkynyl-derivatized sugar.

As used herein, the terms "alkynyl fucose," "alkynyl Fuc" and "Fucyne" are used interchangeably.

As used herein, the term "alkynyl N-acetylmannosamine," "alkynyl ManNAc" and "ManNAcyne" are used interchangeably.

As used herein, the term "alkynyl sialic acid," "alkynyl NeuAc" and "NeuAcyne" are used interchangeably.

As used herein, the term "antibody" means proteins that are found in blood or other bodily fluids of vertebrates, and are used by the immune system to identify and neutralize foreign objects, such as bacteria and viruses.

As used herein, the term "azido-derivatized" means a molecule in which at least one carbon is substituted with an azido functional group.

Amino acid residues in peptides shall hereinafter be abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is H is or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W. H. Freeman & Co., New York 1983.

As used herein, the term "bioorthogonal" means chemical reactants and reactions that are compatible with living systems. Bioorthogonal reactions proceed in high yield under physiological conditions and result in covalent bonds between reactants that are otherwise stable in these settings.

As used herein, the term "bioorthogonal chemical reporting group" means a non-native, non-perturbing, inert chemical functional group, which can be modified in biological systems by chemo-selective reactions with exogenously delivered probes.

As used herein, the term "binding moiety" means a moiety or functional group capable of binding to a second chemical entity.

As used herein, the term "cellular glycan" or "cell glycan" refers to a glycan (either alone or as part of a glycoconjugate) that may be at the cell surface, intracellular, or within a cell lysate.

As used herein, the term "capable of producing" means that a cell is able to perform the designated biochemical function via a known or unknown biosynthetic pathway; for example, many cells are able to produce glycosylated proteins through the FucT salvage pathway.

As used herein, the term "capturing" means chemically linking a molecule of interest with a physical support, wherein the molecule of interest is immobilized.

As used herein, the term "chemoselective" means the preferential reaction of a chemical reagent with only one out of two or more different available functional groups.

As used herein, the term "coumarin" means any of a group of fluorogenic compounds related to benzopyrone or 2-chromenone that are capable of fluorescence modulation dependent on position of substitution and identity of functional groups.

As used herein, the term "conjugate portion" means a non-sugar portion of a glycoconjugate.

As used herein, the term "covalently displaying" means

As used herein, the term "click-activated" means any reaction that bioorthogonally proceeds in a manner that changes the chemical and/or physical properties of the resultant molecule.

As used herein, the term "cycloaddition" means a chemical cyclization reaction, in which two π bonds are lost and two σ bonds are gained—the reaction can proceed catalyzed or uncatalyzed or in a concerted or stepwise manner.

As used herein, the term "differential modification of +1 Da" means an amino acid that may bear a chemical modification resulting in a molecular weight shift of 1 dalton (Da). For example, a Asn residue with a N-linked bond to a glycan can be hydrolyzed to Asp, resulting in a +1 Da change in molecular weight. A differential modification is added to searching algorithms for MS peptide sequencing when all residues of a particular amino acid are not modified (e.g., only Asn residues formerly covalently bound to a glycan will have the +1 Da differential modification). Searching with a diff mod determines if and where a shift from the Asn residue to an Asp residue has occurred, and therefore assigns formerly N-glycosylated sites.

As used herein, the term "derivatization" is used to describe a technique used in chemistry which transforms a chemical compound into a product of similar chemical structure, called a derivative. For example, when reference is made to a sugar analog or precursor that has been "derivatized" with an alkyne group, it is meant that the sugar analog is bearing an alkynyl group.

As used herein, the term "determining" means measuring (qualitatively or quantitatively) a chemical or physical characteristic of a sample of interest.

As used herein, the term "differential analysis" means assessment of relative quantities and identities of proteomes as compared among heterogenous samples or organisms.

As used herein, the term "epitope" means the part of a macromolecule that is recognized by the immune system, specifically by antibodies, B cells, or T cells.

As used herein, the term "flow cytometry" or "FACS" means a technique for examining the physical and chemical properties of particles or cells suspended in a stream of fluid, through optical and electronic detection devices.

As used herein, the term "fluorescent labeled" means derivatizing a molecule with a fluorescent material.

As used herein, the term "fluorogenic" or "fluorescent reporting group" means a material capable of supporting a chemical reaction dependent on the presence of a particular analyte material. Said analyte-dependent chemical reaction produces a fluorescent reporting molecule.

As used herein, the term "fluorescent" means a material exhibiting fluorescence.

As used herein, the term "fucose" is interchangeable with its abbreviation (Fuc) and means a six-carbon deoxy pyran sugar, distinguished from other hexoses by a L-configuration and an unsubstituted carbon at the 6-position.

As used herein, the term "fucosyltransferase (FucT)" means an enzyme that transfers a fucose from a donor substrate, GDP-fucose (GDP=Guanosine diphosphate), to an acceptor substrate, a glycoconjugate or glycan.

As used herein, the term "fucosylated" means a molecule (typically a glycoconjugate or glycan) that has been covalently appended with a Fuc residue (typically by a FucT).

As used herein, the term "functional group" (or "moiety") means a specific group of atoms within molecules that are responsible for the characteristic chemical reactions of those molecules. The same functional group will undergo the same or similar chemical reaction(s) regardless of the size of the molecule it is a part of. However, its relative reactivity can be modified by nearby functional groups.

As used herein, the term "GDP analog" means a molecular derivative of Guanosine diphosphate (GDP).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans are typically comprised of monosaccharides linked together with O-glycosidic bonds. For example, cellulose is a glycan (or more specifically a glucan) composed of beta-1,4-linked D-glucose, and chitin is a glycan composed of beta-1,4-linked N-acetyl-D-glucosamine. Glycans can be homo or heteropolymers of monosaccharide residues, and can be linear or branched. Glycans can be found attached to lipids and proteins, as in glycoproteins and proteoglycans. They are generally found on the exterior surface of cells. O- and N-linked glycans are very common in eukaryotes but may also be found, although less commonly, in prokaryotes. N-linked glycans are attached through amide bonds to asparagine residues found in the N-glycosylation consensus sequon. The sequon is a Asn-X-Ser or Asn-X-Thr sequence, where X is any amino acid except proline. O-linked glycans are attached through glycosidic bonds with oxygen groups on serine and threonine residues in proteins, or hydroxyl groups of lipids and small molecules.

As used herein, the term "glycoconjugate" means a molecule covalently modified with glycans.

As used herein, the term "glycoprotein" means a protein covalently modified with glycan(s). There are four types of glycoproteins: 1) N-linked glycoproteins, 2) O-linked glycoproteins (mucins), 3) glucosaminoglycans (GAGs, which are also commonly called proteoglycans), 4) GPI-anchored. Most glycoproteins have structural micro-heterogeneity (multiple different glycan structures attached within the same glycosylation site), and structural macro-heterogeneity (multiple sites and types of glycan attachment).

As used herein, the term "glycoproteomics" refers to a branch of proteomics that identifies, catalogs, and characterizes proteins containing carbohydrates as a post-translational modification. Glycoproteomics also refers to the study of a cell, tissue, or organism's glycan and glycoprotein content at any point in time.

As used herein, the term "glycosylation" means the enzymatic transfer of saccharides or oligosaccharide chains onto glycoconjugates. Protein glycosylation is a complex co- or post-translational process that modifies the majority of the human proteome, vastly expanding its functional repertoire.

As used herein, the term "harvesting" means concentrating, collecting, purifying and/or storing a material of interest.

As used herein, the term "isolated" means glycoconjugates that can be selectively separated by secondary detection means.

As used herein, the term "incorporating" means introducing a compound or derivative of a compound into the intracellular environment by any method, including but not limited to inclusion in media or restricted media; electroporation; injection; phagocytosis; active transport; endocytosis; active transport; passive transport; carrier-assisted transport; vesicle-mediated transport; and diffusion.

As used herein, the term "labeled glycoprotein" means a glycoprotein covalently attached via cycloaddition to a moiety that can facilitate the manipulation of the "labeled glycoprotein," such as the isolation, visualization, detection, and quantification of the labeled glycoprotein.

As used herein, the term "liquid chromatography-mass spectrometry" or "LC-MS" refers to an analytical chemistry technique that combines the physical separation capabilities of liquid chromatography (aka HPLC) with the mass analysis capabilities of mass spectrometry (MS). LC-MS is a powerful technique used for many applications which has very high sensitivity and specificity. Generally its application is oriented towards the specific detection and potential identification of chemicals in the presence of other chemicals (in a complex mixture). LC-MS is also used in the study of proteomics where components of a complex mixture must be detected and identified in some manner. The bottom-up proteomics LC-MS approach to proteomics generally involves protease digestion (usually Trypsin) followed by LC-MS with peptide mass fingerprinting or LC-MS$^2$ (tandem MS) to derive the sequence of individual peptides.

As used herein, the term "metabolic oligosaccharide engineering" or "MOE" means the process of incorporating an alkynyl-derivatized sugar into a glycoconjugate.

As used herein, the term "MudPIT" or Multidimentional Protein Identification Technology refers to the characterization of protein mixtures using tandem LC-MS$^2$. A peptide mixture that results from digestion of a protein mixture is fractionated by multiple steps of liquid chromatography. The eluent from the chromatography stage can be either directly introduced to the tandem MS through electrospray ionization, or laid down on a series of small spots for later mass analysis using MALDI.

As used herein, the term "proteome" refers to the entire complement of proteins expressed by a genome, cell, tissue or organism. More specifically, it is the expressed proteins at a given time point under defined conditions.

As used herein, the term As used herein, the term "presenting" means introducing into the extracellular environment, including, but not limited to, inclusion in growth media, restricted media, reaction solution, buffer, and/or staining solution.

As used herein, the term "proteomics" refers to the study of the proteome. Proteomics has largely been practiced through the separation of proteins by two dimensional gel electrophoresis. In the first dimension, the proteins are separated by isoelectric focusing, which resolves proteins on the basis of charge. In the second dimension, proteins are separated by molecular weight using SDS-PAGE. The gel is dyed with Coomassie Blue or silver stain to visualize the proteins. Spots on the gel are proteins that have migrated to specific locations. The mass spectrometer has augmented proteomics. Peptide mass fingerprinting identifies a protein by cleaving it into short peptides and then deduces the protein's identity by matching the observed peptide masses against a sequence database. Tandem mass spectrometry, on the other hand, can get sequence information from individual peptides by isolating them, colliding them with a non-reactive gas, and then cataloging the fragment ions produced.

As used herein, the term "pulse-chase" means a method for examining a cellular process occurring over time by successively exposing the cells to a labeled compound (pulse) and then to the same compound in nonlabeled form (chase).

As used herein, the term "reacting" means inducing a chemical reaction between two or more substances, including, but not limited to, catalyzing such reaction and providing appropriate supporting reaction substituents to maintain biochemical pH and thermodynamic environments.

As used herein, the term "reporting group" means a molecule that has properties capable of presenting detectable feedback about events transpiring in a test system (from a controlled in vitro assay to a complex biological system).

As used herein, the term "sialylated" means a molecule (typically a glycoconjugate or glycan) that has been covalently appended with a sialic acid (NeuAc) residue (typically by a sialyl transferase)

As used herein, the term "tagged" means a glycoconjugate that has incorporated an alkynyl-derivatized sugar through any permissive biosynthetic pathway involved in glycoconjugate synthesis.

As used herein, the term "toxicity" means the relative percentage of cells (assayed by any method of cell counting) surviving 3 days in vitro or in vivo after addition of sugar analogs (natural and/or derivatized) compound to the relevant cellular environment.

As used herein, the term "trafficking" means the movement of material from one location to another within, into, or out of a cell, and any associated modifications of the material occurring in the process.

In one exemplary implementation, the disclosure provides a method of labeling glycoconjugates in a cell, the method comprising: presenting an alkynyl-derivatized sugar; incorporating the alkynyl-derivatized sugar into glycoconjugates in the cell by growing the cell in the presence of the alkynyl-derivatized sugar to create an tagged glycoconjugate (alkynyl-tagged glycoconjugate); contacting the tagged glycoconjugate with a chemical probe wherein said chemical probe reacts with said alkynyl group in the tagged glycoconjugate to create a labeled, tagged glycoconjugate; and manipulating the labeled, tagged glycoconjugate for further analysis. Analysis can include detecting labeled alkynyl-derivatized-tagged glycoconjugates through fluorescence to determine one or more of the location and relative abundance; or isolating them to determine their identity and relative abundance.

In one exemplary implementation, the disclosure provides a method of labeling fucosylated glycoconjugates in a cell, the method comprising: presenting an alkynyl-derivatized fucose; tagging a glycoconjugate in the cell by growing the cell in the presence of an alkynyl-derivatized fucose to create an alkynyl-tagged fucosylated glycoconjugate; labeling the alkynyl-tagged glycoconjugate with a chemical probe which will bind covalently to the alkynyl group to create a labeled-glycoconjugate; and detecting the labeled, tagged glycoconjugate to determine that the labeled-glycoconjugate in the cell is a fucosylated glycoconjugate.

In another exemplary implementation, the disclosure provides a method of identifying a sialylated glycoconjugate in a cell, the method comprising: presenting an alkynyl-derivatized N-acetylmannosamine; tagging a glycoconjugate in the cell by growing the cell in the presence of alkynyl-derivatized N-acetylmannosamine to create a tagged, sialylated alkynyl-derivatized glycoconjugate; labeling the alkynyl-derivatized glycoconjugate with a chemical probe which will bind covalently to the alkynyl group to create a labeled, tagged glycoconjugate; and detecting the labeled-glycoconjugate to determine that the labeled-glycoconjugate in the cell is a sialylated glycoconjugate.

In a further exemplary implementation, the disclosure provides a method of incorporating an alkynyl derivatized sugar into a glycoconjugate in a cell, the method comprising: presenting an alkynyl-derivatized sugar; and tagging a glycoconjugate in the cell by growing the cell in the presence of the alkynyl-derivatized sugar to create an labeled, tagged glycoconjugate.

In one exemplary implementation, the alkynyl-derivatized sugar tagged glycoconjugate is a fucosylated glycoconjugate and the alkynyl-derivatized sugar is an alkynyl-derivatized fucose. In a specific exemplary implementation, the alkynyl-derivatized fucose is 1,2,3,4-tetraacetyl alkynyl fucose.

In another exemplary implementation, the tagged glycoconjugate is a sialylated-glycoconjugate and the alkynyl-derivatized sugar is an alkynyl-derivatized N-acetylmannosamine. In a specific exemplary implementation, the alkynyl-derivatized N-acetylmannosamine is 1,3,4,6-tetra-O-acetyl-N-4-pentynoylmannosamine.

In another exemplary implementation, the disclosure provides a method of detecting an alkynyl-tagged glycoconjugate, the method comprising: contacting the alkynyl-derivatized sugar tagged glycoconjugate with a chemical probe wherein said chemical probe reacts with said alkynyl group in the alkynyl-derivatized sugar-tagged glycoconjugate to create a labeled, tagged glycoconjugate; and detecting the labeled, tagged glycoconjugate to determine one or more of the location and the abundance of the labeled-glycoconjugate in the cell. In one exemplary implementation, the contacting step is performed on a cell surface, on a permeabilized cell, or on a cellular extract.

In one exemplary implementation, the disclosure provides a method of metabolic oligosaccharide engineering (MOE) that incorporates derivatized alkyne-bearing sugar analogs into cellular glycoconjugates, thereby creating alkynyl-tagged glycoconjugates.

In one exemplary implementation, the alkyne-derivatized sugar analogs utilized in MOE are minimally toxic to the cell.

In one exemplary implementation, the alkyne-derivatized sugar analogs utilized in MOE minimally alter the cell's normal proteosome glycosylation pattern.

In one exemplary implementation, the derivatized alkynyl sugars are peracetylated.

In one exemplary implementation, the derivatized alkynyl sugars are acetylated.

In one exemplary implementation, the derivatized alkynyl sugars are derivatized fucose (Fuc).

In one exemplary implementation, the derivatized alkynyl sugars are fucose analog precursors capable of subsequent intracellular derivatization and subsequent incorporation into cellular, cell surface and/or extracellular fucosylated glycoconjugates.

In one exemplary implementation, the derivatized alkynyl sugars are sialic acid precursors capable of subsequent derivatization and incorporation into cellular, cell surface and/or extracellular sialylated glycoconjugates.

In one exemplary implementation, the derivatized alkynyl sugars are ManNAcyne.

In one exemplary implementation, the derivatized alkynyl sugars are NeuACyne.

In one exemplary implementation, the derivatized alkynyl sugars are Fucyne.

In one exemplary implementation, the derivatized alkynyl sugars are metabolic precursors to derivatized fucose and sialic acid analogues capable of subsequent intracellular metabolic incorporation into fucosylated and/or sialylated glycoconjugates.

In one exemplary implementation, the derivatized alkynyl sugars are capable of metabolic incorporation into fucosylated and/or sialylated glycoconjugates where they are subsequently capable of azido-alkynyl cycloaddition covalent binding with an azido-derivatized probe so as to create a labeled, tagged glycoconjugate.

In one exemplary implementation, the derivatized alkynyl sugars are bioorthogonal.

In one exemplary implementation, derivatized alkynyl sugars are incorporated into glycoconjugates.

In one exemplary implementation, derivatized alkynyl sugars are incorporated into glycoconjugates at the terminal position.

In one exemplary implementation, derivatized alkynyl sugars are incorporated into fucosylated glycoconjugates.

In one exemplary implementation, derivatized alkynyl sugars are incorporated into sialylated glycoconjugates.

In one exemplary implementation, derivatized alkynyl sugars capable of fluorescence by further derivatization are incorporated into glycoconjugates.

In one exemplary implementation, derivatized alkynyl sugars are incorporated into glycoproteins.

In one exemplary implementation, derivatized alkynyl sugars are incorporated into glycolipids.

In one exemplary implementation, the glycoconjugate is a fucosylated glycoconjugate or a sialylated glycoconjugate.

In another exemplary implementation, the glycoconjugate is a fucosylated glycoconjugate and the alkynyl-derivatized sugar originates from an alkynyl-derivatized fucose in the cell by MOE. In a specific exemplary implementation, the alkynyl-derivatized fucose is 1,2,3,4-tetraacetyl alkynyl fucose.

In one exemplary implementation, the alkynyl-tagged glycoconjugate is a sialylated-glycoconjugate and the alkynyl-derivatized sugar originates from alkynyl-derivatized N-acetylmannosamine in the cell by MOE.

In a specific exemplary implementation, the alkynyl-derivatized N-acetylmannosamine is 1,3,4,6-tetra-O-acetyl-N-4-pentynoylmannosamine.

In another exemplary implementation, the MOE sugar incorporating step further comprises growing the cell in the presence of the alkynyl-derivatized fucose, from about 1 to about 1000 micromolar concentrations in the growth medium.

In another exemplary implementation, the MOE sugar incorporating step comprises growing the cell in the presence of the alkynyl-derivatized N-acetylmannosamine, from about 1 to about 100 micromolar concentration in the growth medium.

In one exemplary implementation, the labeled-glycoconjugate is a cellular glycoconjugate located on the surface of the cell. In another exemplary implementation, the method further comprises treating the cell to permeabilize the cell prior to the contacting step.

In another exemplary implementation, azide bearing probes additionally comprising one or more of biotin and coumarin groups are bound covalently to alkynyl-tagged glycoconjugates to provide labeled glycoconjugates.

In one exemplary implementation, tagged glycoconjugates are capable of subsequent chemoselective labeling.

In one exemplary implementation, tagged glycoconjugates are labeled with a probe by azide-alkyne cycloaddition.

In one exemplary implementation, the probe is fluorogenic.

In one exemplary implementation, tagged glycoconjugates are labeled with a probe by CuAAC.

In one exemplary implementation, tagged glycoconjugates are labeled with a probe by azide-alkyne cycloaddition so as to generate a triazole moiety at the tagged glycoconjugate-probe interface.

In one exemplary implementation, tagged glycoconjugates are labeled with a probe by azide-alkyne cycloaddition so as to generate a triazole moiety at the tagged glycoconjugate-probe interface in aqueous solutions.

In one exemplary implementation, tagged glycoconjugates are labeled with a probe by azide-alkyne cycloaddition so as to generate a triazole moiety at the tagged glycoconjugate-probe interface at biologically relevant pH.

In one exemplary implementation, tagged glycoconjugates are labeled with a probe by azide-alkyne cycloaddition so as to generate a triazole moiety at the tagged glycoconjugate-probe interface while maintaining bioorthogonality of the reaction components and products.

In one exemplary implementation, tagged glycoconjugates are labeled with a probe by azide-alkyne cycloaddition so as to generate a triazole moiety at the tagged glycoconjugate-probe interface at biological pH.

In one exemplary implementation, tagged glycoconjugates are labeled with a probe by azide-alkyne cycloaddition so as to generate a triazole moiety at the tagged glycoconjugate-probe interface with nearly quantitiative reaction efficiency.

In one exemplary implementation, the probe is an azido-derivatized probe.

In one exemplary implementation, the probe is a coumarin.

In one exemplary implementation, the probe is biotin.

In one exemplary implementation, the probe additionally includes an secondary binding label.

In one exemplary implementation, the probe is additionally capable of being isolated or quantified directly.

In one exemplary implementation, the probe is additionally capable of being isolated or quantified indirectly through use of secondary binding/detection means.

In one exemplary implementation, the probe is additionally capable of being isolated or quantified through use of antibody-antigen interactions.

In one exemplary implementation, the probe is additionally capable of being isolated or quantified through use of lectin-glycan interactions.

In one exemplary implementation, the probe is additionally capable of being isolated or quantified through use of streptavidin/avidin-biotin binding.

In one exemplary implementation, the probe is additionally capable of being isolated or quantified through use of a fluorophore.

In a further exemplary implementation, a variety of techniques are disclosed for visualization of the labeled cellular glycoconjugate.

In one exemplary implementation, labeled, tagged glycoconjugates are visualized on the cell surface of a eukaryotic or prokaryotic cell.

In one exemplary implementation, labeled, tagged glycoconjugates are isolated.

In one exemplary implementation, labeled, tagged glycoconjugates are visualized.

In one exemplary implementation, labeled, tagged glycoconjugates are isolated through streptavidin/avidin-biotin interactions.

In one exemplary implementation, labeled, tagged glycoconjugates are isolated through antibody-antigen interactions.

In one exemplary implementation, labeled, tagged glycoconjugates are visualized through azide-alkyne cycloaddition-mediated fluorescence.

In one exemplary implementation, labeled, tagged glycoconjugates are quantified through azide-alkyne cycloaddition-mediated fluorescence.

In one exemplary implementation, the chemical probe comprises an azide group. In a specific exemplary implementation, the chemical probe binds covalently to the alkynyl group in tagged-glycoconjugates by CuAAC, thereby creating labeled-glycans.

In one exemplary implementation, the chemical probe further comprises one of a visualizable probe and a fluorogenic probe. In one exemplary implementation, the visualizable probe comprises a biotin group. In another exemplary implementation, the fluorogenic probe comprises a coumarin group.

In one exemplary implementation, the detecting step comprises visualizing the labeled glycoconjugate by one or more techniques of flow cytometry, SDS-PAGE, Western blot, ELISA, confocal microscopy, and mass spectrometry. In another exemplary implementation, the detecting step further comprises quantifying the labeled-glycoconjugate by one or more techniques of flow cytometry, SDS-PAGE, Western blot, ELISA and confocal microscopy.

In one exemplary implementation, derivatized sugars are presented to a cell for a limited time, and succeeded by presenting the cell with non-derivatized sugars.

In one exemplary implementation, derivatized sugars are presented to a cell for a limited time, and both preceded and succeeded by presenting the cell with non-derivatized sugars.

In one exemplary implementation, the derivatized sugars are subsequently labeled and detected at various time intervals subsequent to the limited presentment of such sugars to the cell.

In one exemplary implementation, the various time interval detections of derivatized sugars are compared so as to assess cellular trafficking of glycoconjugates.

In one exemplary implementation, the various time interval detections of derivatized sugars are compared so as to assess differential cellular trafficking of glycoconjugates.

In one exemplary implementation, the various time interval detections of derivatized sugars are compared with various interval detections of the location of various intracellular and extracellular bodies (e.g. nucleus, Golgi apparatus, lysosome) so as to assess differential cellular trafficking of glycoconjugates.

In one exemplary implementation, derivatized sugars are presented to a cell for a limited time are alkynyl-derivatized sugars.

In one exemplary implementation, the derivatized sugars presented to a cell for a limited time are alkynyl-derivatized sugars.

In one exemplary implementation, the derivatized sugars presented to a cell for a limited time are azido-derivatized sugars.

In one exemplary implementation, the derivatized sugars presented to a cell for a limited time are both alkynyl and azido-derivatized sugars.

In one exemplary implementation, the derivatized sugars presented to a cell for a limited time are incorporated into fucosylated glycoconjugates.

In one exemplary implementation, the derivatized sugars presented to a cell for a limited time, preceded and succeeded by presenting the cell with non-derivatized sugars are incorporated into sialylated glycoconjugates.

In one exemplary implementation, the derivatized sugars presented to a cell for a limited time, preceded and succeeded by presenting the cell with non-derivatized sugars are incorporated into both fucosylated and sialylated glycoconjugates.

In one exemplary implementation, the derivatized sugars presented to a cell for a limited time, preceded and succeeded by presenting the cell with non-derivatized sugars are presented to the cells with CuAAC catalysts.

In one exemplary implementation, the derivatized sugars presented to a cell for a limited time, preceded and succeeded by presenting the cell with non-derivatized sugars are presented to the cells without CuAAC catalysts.

Herein disclosed, alkynyl Fuc and alkynyl ManNAc analogs are synthesized and utilized as reporting saccharides in a method to tag fucosylated and sialylated glycoconjugates in mammalian cells. Previously, a fluorescent labeling technique for probing metabolically labeled fucosylated glycoconjugates in cells was reported by this laboratory.

In the previous approach, derivatized azido Fuc analogs incorporated into glycoconjugates were labeled with a 1,8-naphthalimide fluorogenic probe, by using Cu(I)-catalyzed azide-alkyne [3+2]cycloaddition, or alkyne-azide "click" reaction. The click-activated fluorescent labeling was used for specifically utilizing azido-derivatized labels to label alkynyl-derivatized, sugar-tagged fucosylated and sialylated glycoconjugates, and is also effective for use in so-called "pulse-chase" applications where there is limited presentment of the azido-derivatized sugar to the cell, and/or the presentment of the azido-derivatized sugar to the cell is in low concentration. In the present method, alkynyl Fuc and alkynyl ManNAc analogs show reduced toxicity to cells when compared with azido Fuc analogs. Moreover, when these alkynyl derivatized sugars are coupled with biotin, click-activated fluorogenic coumarin, and other fluorescent probes, this method allows for the isolation of fucosylated and sialylated glycoconjugates for further analysis, and fluorescent imaging (where alkynyl sugar labeling causes less background signal). This method can be used for visualizing glycan dynamics inside of cells and to identify important glycan markers.

Scheme 1. Modified sugar analogs and probes.

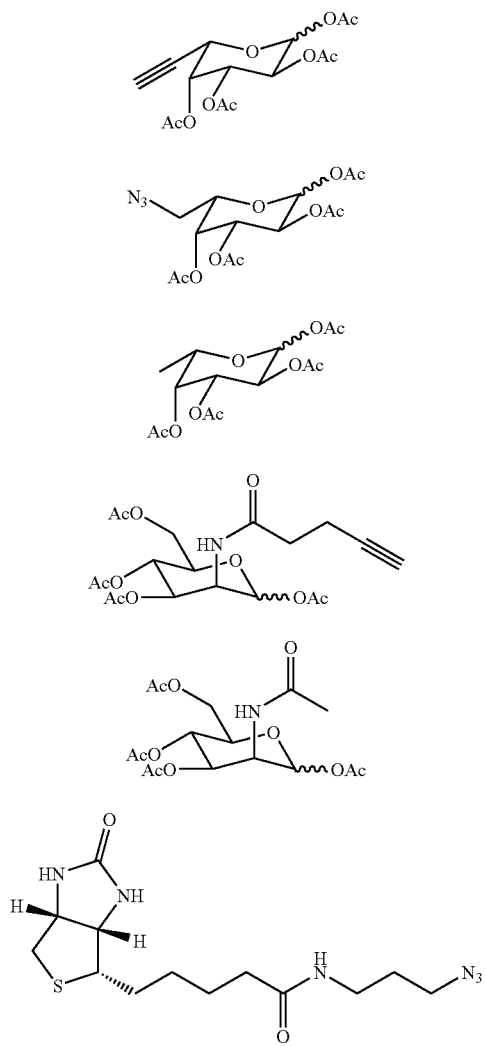

-continued

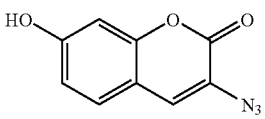

7

Synthesis of Alkynyl Sugars and Biotinylated Azide Probe.

In one exemplary implementation of the disclosure, an Intermediary of Alkynyl Derivatized Fucose is 1,2:3,4-Di-O-isopropylidene-□-L-galactose To L-galactono-1,4-lactone (10 g, 56.1 mmol) in MeOH (60 mL) and water (250 mL) at 0° C. was added Amberlite IR 120 (H⁺) resin (50 mL). NaBH₄ (2.2 g, 56.1 mmol) was added portionwise, and the reaction mixture was stirred for 1 h at room temperature. The resin was removed by filtration, and the filtrate was evaporated. The residue was dissolved in acetone (220 mL), CuSO₄ (22.2 g, 0.14 mol) and H₂SO₄ (1 mL) was added and the solution was stirred at room temperature overnight. The CuSO₄ was removed by filtration, and the filtrate was neutralized with Ca(OH)₂. After removal of Ca(OH)₂ and concentration, the residue was purified by flash column chromatography on silica gel (AcOEt/hexane 1:1) to afford 17 (9.1 g, 62%).

In one exemplary implementation of the disclosure, per-acetylated alkynyl derivatives of Fuc 1 andManNAc 4, shown in Scheme 1, are synthesized and used to tag fucosylated and sialylated glycoconjugates, respectively, in vivo. The sugar derivatives are synthesized in their peracetylated forms, as this modification is known to increase their cellular uptake efficiency. The acetate esters are subsequently hydrolyzed in the cytosol.

In one aspect of the disclosure, the synthesis of alkynyl Fuc (1, see Example 1, Scheme 2) proceeds from a known four-step transformation, beginning with 1-(+)-galactonic acid □-lactone and ending with the alkynyl diisopropylidene-Fuc intermediate. Subsequent protecting group removal followed by acetylation of the intermediate yields the desired compound 1, as a mixture of pyranoside and furanoside forms. This mixture is used directly for labeling fucosylated glycoconjugates in cells.

Scheme 2.

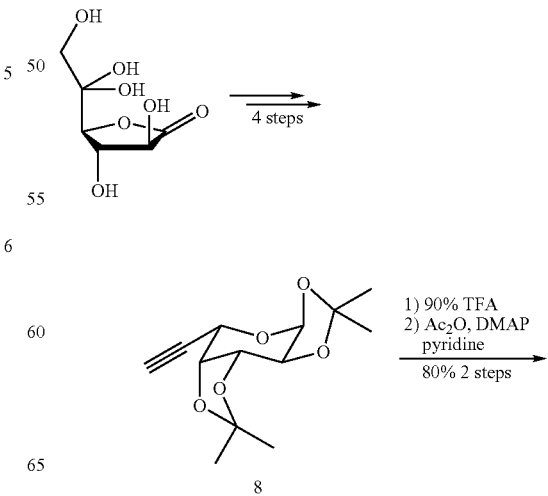

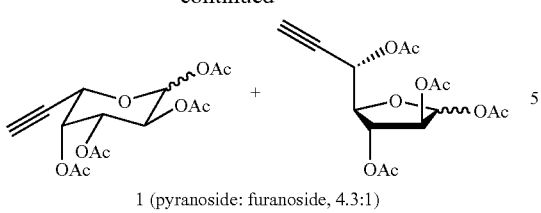

1 (pyranoside: furanoside, 4.3:1)

In another aspect of the disclosure, compound 4 is synthesized and used for tagging sialylated glycoconjugates. D-Mannosamine hydrochloride is reacted with N-succinimidyl 4-pentynoate in triethylamine to yield alkynyl ManNAc derivative (see Example 2, Scheme 3). The alkynyl ManNAc 4 is subsequently obtained by acetylation.

Scheme 3.

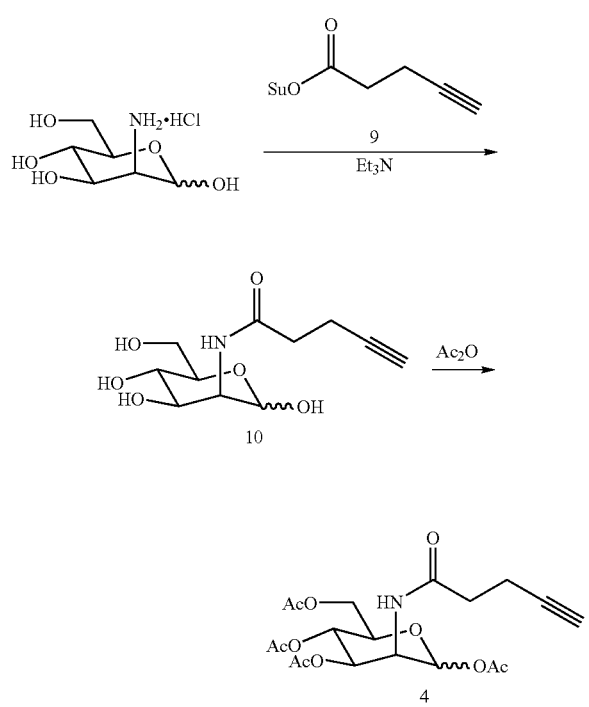

The coupling partner, biotinylated azido probe 6, is synthesized by coupling of biotin to 1-azido-3-aminopropane (see Example 4, Scheme 4). Fluorogenic probe 7, 3-azido-7-hydroxycoumarin, is synthesized as reported. Modified sugar analogs and probes used in this study are illustrated in Scheme 1.

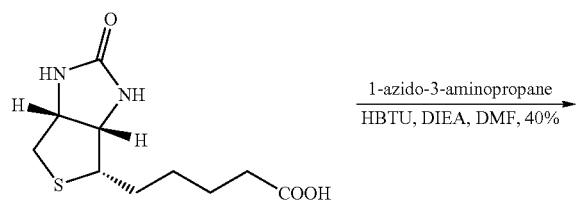

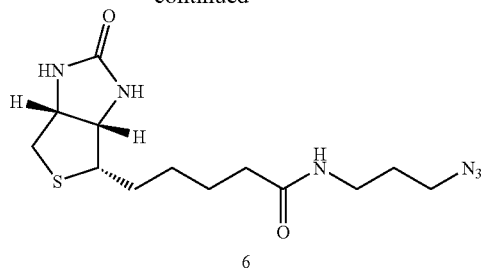

6

Fluorescent Labeling of Alkynyl Glycoconjugates at the Cell Surface.

In another exemplary implementation, a method for labeling fucosylated glycoconjugates at the cell surface is disclosed. In one aspect, Jurkat cells are grown in the presence of derivatized alkynyl Fuc 1. After treatment, cells are subjected to CuAAC (click chemistry) to couple biotinylated azido probe 6 with any alkynyl Fuc-bearing glycoconjugates, and stained with fluorescein-conjugated streptavidin.

Labeling alkynyl Fuc-bearing cell surface glycoconjugates is illustrated in FIG. 1. FIG. 1 shows analysis of cells tagged with Fuc analogs analyzed by monitoring fluorescence intensity with flow cytometry after labeling with a biotin azide probe 6 and staining cells with fluorescein-conjugated streptavidin. As shown in FIG. 1A, the derivatized alkynyl Fuc 1-treated cells show increased fluorescence intensity compared with control Fuc 3-treated cells, as analyzed by flow cytometry. This indicates that alkynyl-derivatized Fuc residues are incorporated into ("tag") cell surface glycoconjugates and that these tags can serve as binding sites for chemoselective cycloaddition labeling. Without being bound by theory, incorporation of the derivatized Fuc analogs into fucosylated glycoconjugates likely occurs via the Fuc salvage pathway. Alkynyl Fuc analog 1-treated cells showed a dose dependent increase of fluorescence signal, with a 3-fold greater mean fluorescence intensity (MFI) compared with Fuc treated cells at 200 micromolar concentration (FIG. 1B). The data also showed saturation of alkynyl Fuc 1 incorporation within one-day of incubation, although there was a slight increase of labeling signal on cells treated for three days with alkynyl Fuc 1 (FIG. 1C).

Figure 1D:
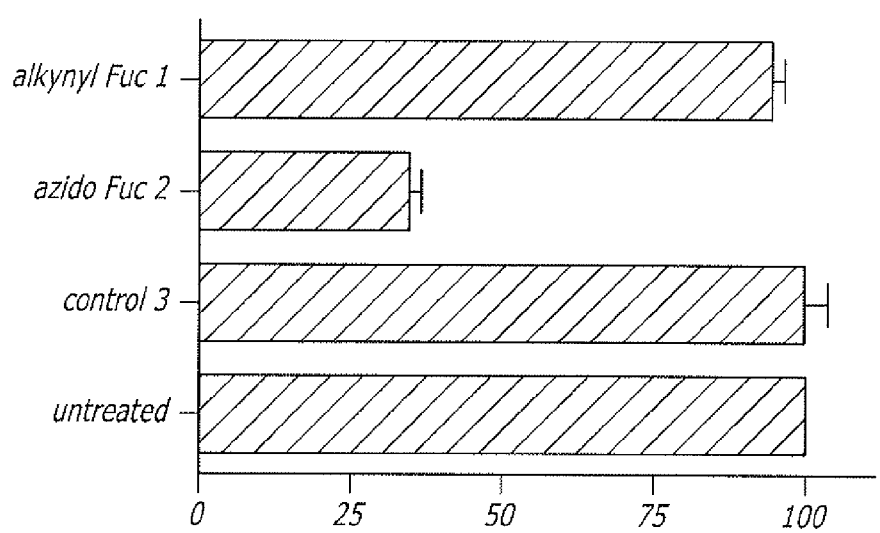
FIG. 1 shows analysis of cells labeled with Fuc analogs

It is also disclosed how treatment with exogenous Fuc analog affects cell growth rate. As shown in FIG. 1D, the number of cells after 3 days is similar whether they are treated with 200 micromolar alkynyl Fuc 1, 200 micromolar Fuc 3, or grown without exogenous Fuc. In contrast, the addition of 200 micromolar azido Fuc 2 inhibits cell growth considerably, by 65% when compared with the untreated cells. These results indicate that azido Fuc 2 analog, which was used previously for probing fucosylation, is more toxic to cells than alkynyl Fuc 1 analog. Such toxicity may lead to global change in expression, therefore a nontoxic probe is preferable for accurate probing of glycoconjugate expression.

Previously, it was demonstrated that the majority of an exogenous ManNAc analog, N-levulinoylmannosamine, acquired by cells is converted into sialic acid via biosynthetic pathways.

Figure 2A:
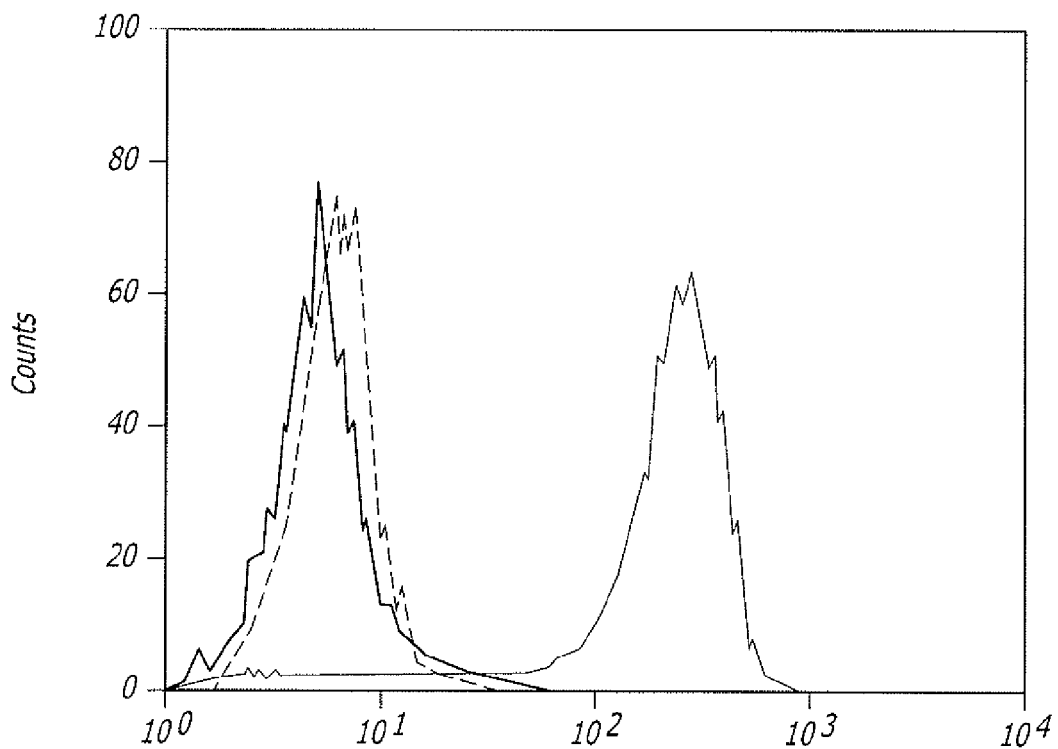
FIG. 2(A) shows flow cytometry analysis of Jurkat cells tagged with derivatized alkynyl-derivatized ManNAc (filled trace, untreated cells; green, cells treated with control 5; purple, cells treated with alkynyl ManNAc 4).
Figure 2B:
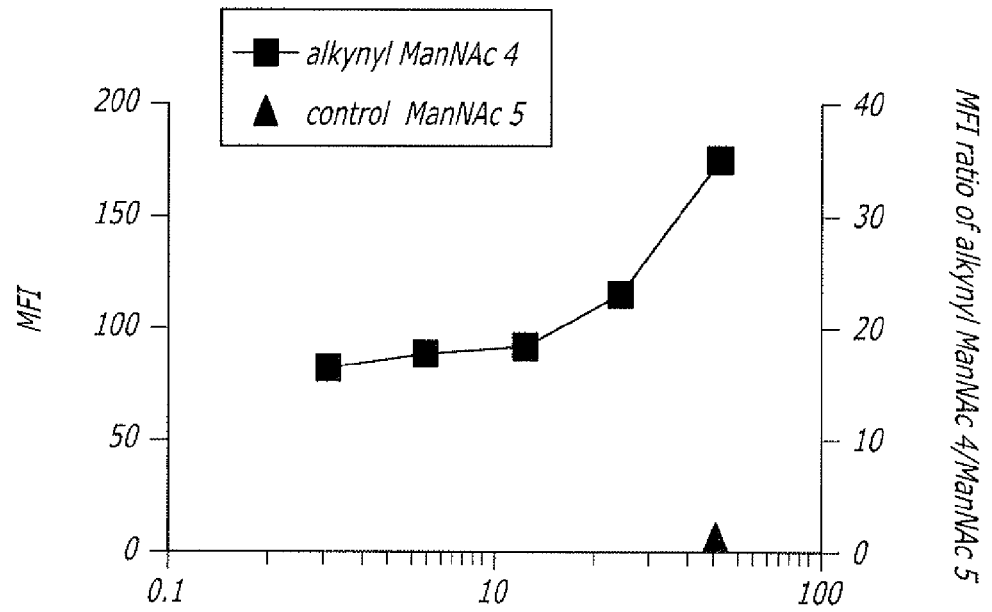
FIG. 2(B) shows dose dependency of sialyl glycoconjugate tagging with alkynyl-derivatized ManNAc 4 for 3 days.
Figure 2C:
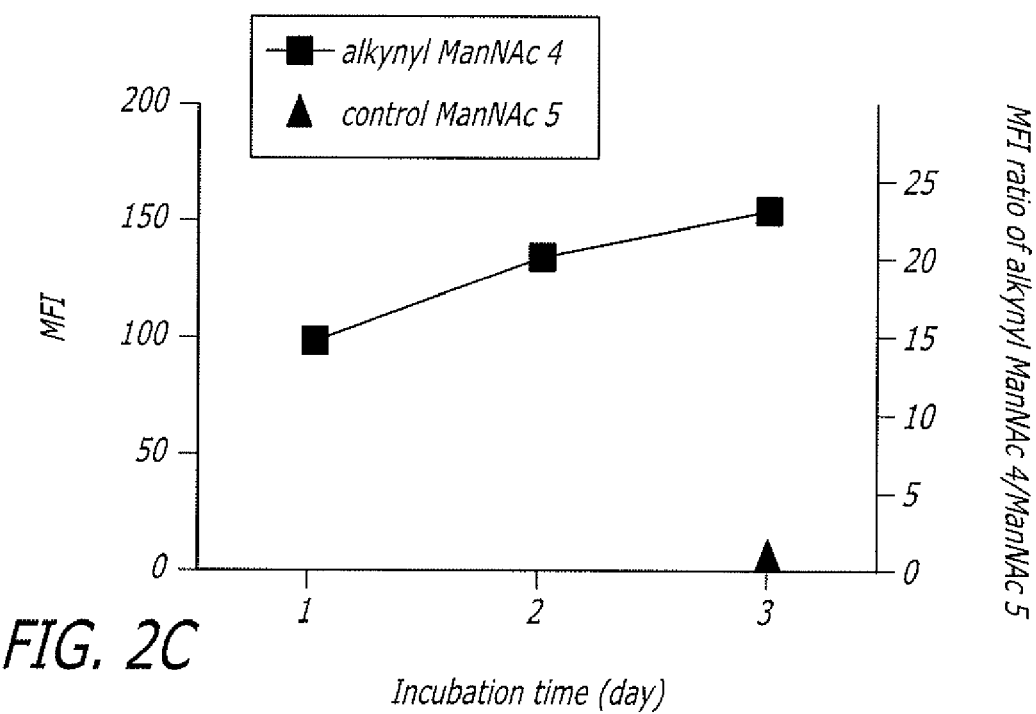
FIG. 2(C) shows time course for tagging sialyl glycoconjugates by treatment with 25 micromolar alkynyl-derivatized ManNAc 4.
Figure 2D:
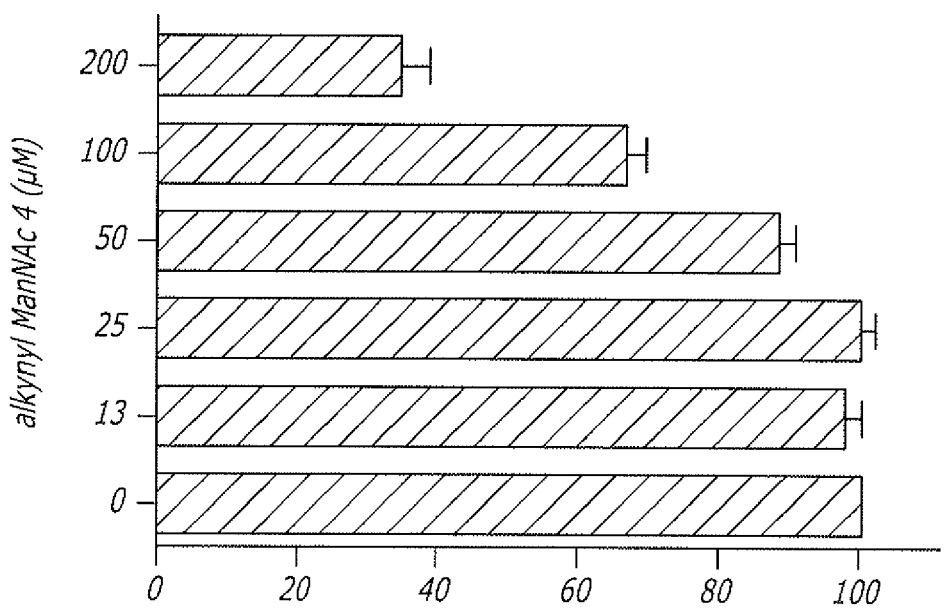
FIG. 2(D) shows growth rate of Jurkat cells treated with different doses of alkynyl-derivatized ManNAc 4 after 3 days.

It is now disclosed in one exemplary implementation of the disclosure that treating cells with derivatized alkynyl ManNAc 4 results in derivatized alkyne-bearing sialyl glycoconjugates. In one aspect of the method, cells are treated with 4 at various concentrations for one to 3 days. Modified sugar analogs and probes used in this disclosure are shown in Scheme 1. Tagging of the cell surface glycoconjugates by derivatized alkynyl ManNAc is illustrated in FIG. 2. FIG. 2 shows analysis of cells labeled with ManNAc analogs analyzed by monitoring fluorescence intensity with flow cytometry after clicking on the biotin azide probe 6 and staining cells with fluorescein-conjugated streptavidin. Labeling with derivatized alkynyl ManNAc 4 yielded a specific signal on the cell surface compared with the control values obtained from cells treated with control ManNAc 5 (FIG. 2A). Dose-dependent labeling was observed in cells treated with derivatized alkynyl ManNAc 4 (FIG. 2B). Compared with the MFI of controls, there was significant labeling on cells treated with derivatized alkynyl ManNAc 4, even at concentrations as low as 3 micromolar (15-fold increase). Time-course experiments revealed that treatment with derivatized alkynyl ManNAc 4 from one to three days gave a 15- to 23-fold increase in labeling intensity over control levels (FIG. 2C). The optimal concentration of 4 for tagging sialyl glycoconjugates falls between 25 and 50 micromolar. In this concentration range, 4 showed little or no toxicity, although it is more toxic above 100 micromolar (FIG. 2D).

One of the advantages of labeling an alkynyl-derivatized sugar tagged glycoconjugate with an azido-derivatized probe via CuAAC, or the click reaction, is the formation of a triazole unit, which can modulate the fluorescent emission of probes through electron-donating properties. It was previously shown that such click-activated fluorescence is useful in fluorescently labeling azido Fuc-bearing glycoconjugates using a 1,8-naphthalimide-alkyne probe. However, the azido version of the naphthalimide probe causes high background, making it less useful for labeling our alkynyl sugars.

Figure 3A:
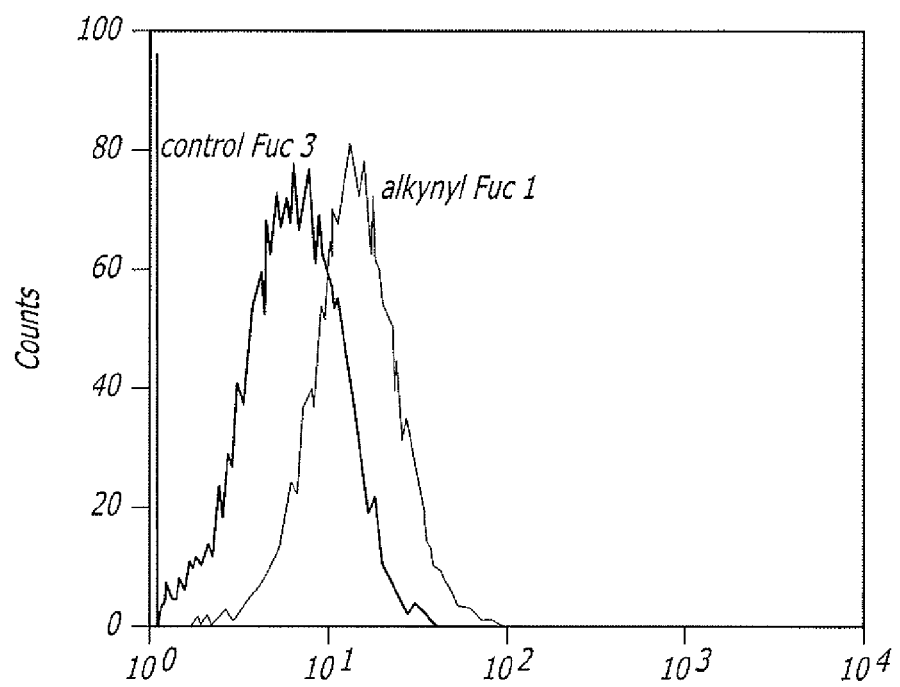
FIG. 3 shows tagging of cell surface glycans by derivatized alkynyl sugar analogs and subsequent labeling with probe 3-azido-7-hydroxycoumarin 7. Shown is flow cytometry analysis of Jurkat cells tagged with 200 micromolar derivatized alkynyl Fuc 1 (A) or 25 micromolar alkynyl-derivatized ManNAc 4 (B) for 3 days. The fluorescence intensity was detected after labeling with a coumarin probe 7. Filled histogram, cells treated with control sugar analog 3 or 5; open histogram, cell treated with alkynyl-derivatized sugar 1 or 4.
Figure 3B:
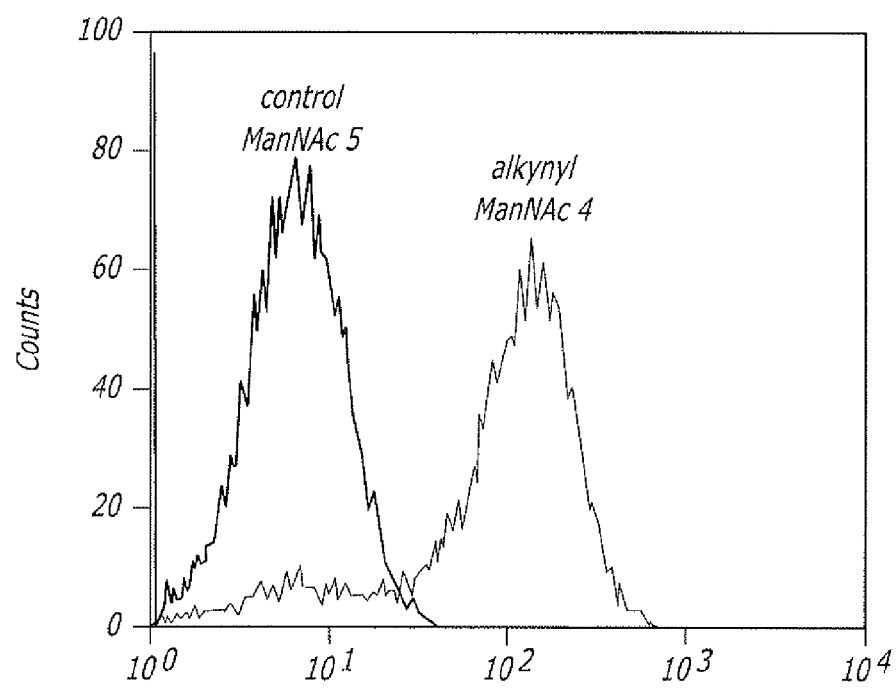

Recently, another click-activated azido-deritatized fluorescent probe, based on coumarin, was reported in the literature. In one aspect of the disclosure, the fluorogenic probe, 3-azido-7-hydroxycoumarin 7, is used as the coupling partner for alkynyl tags on labeled glycoconjugates. As shown in FIG. 3, cells treated with derivatized alkynyl Fuc 1 (FIG. 3A) or derivatized alkynyl ManNAc 4 (FIG. 3B) allowed significant fluorescent labeling after reacting with a 3-azido-7-hydroxycoumarin probe, whereas cells treated with control sugars 3 and 5 gave very low background signals, evidencing low reactivity with a 3-azido-7-hydroxycoumarin probe.

Visualization of Fluorescently Labeled Glycoconjugates in Cells.

Figure 4:
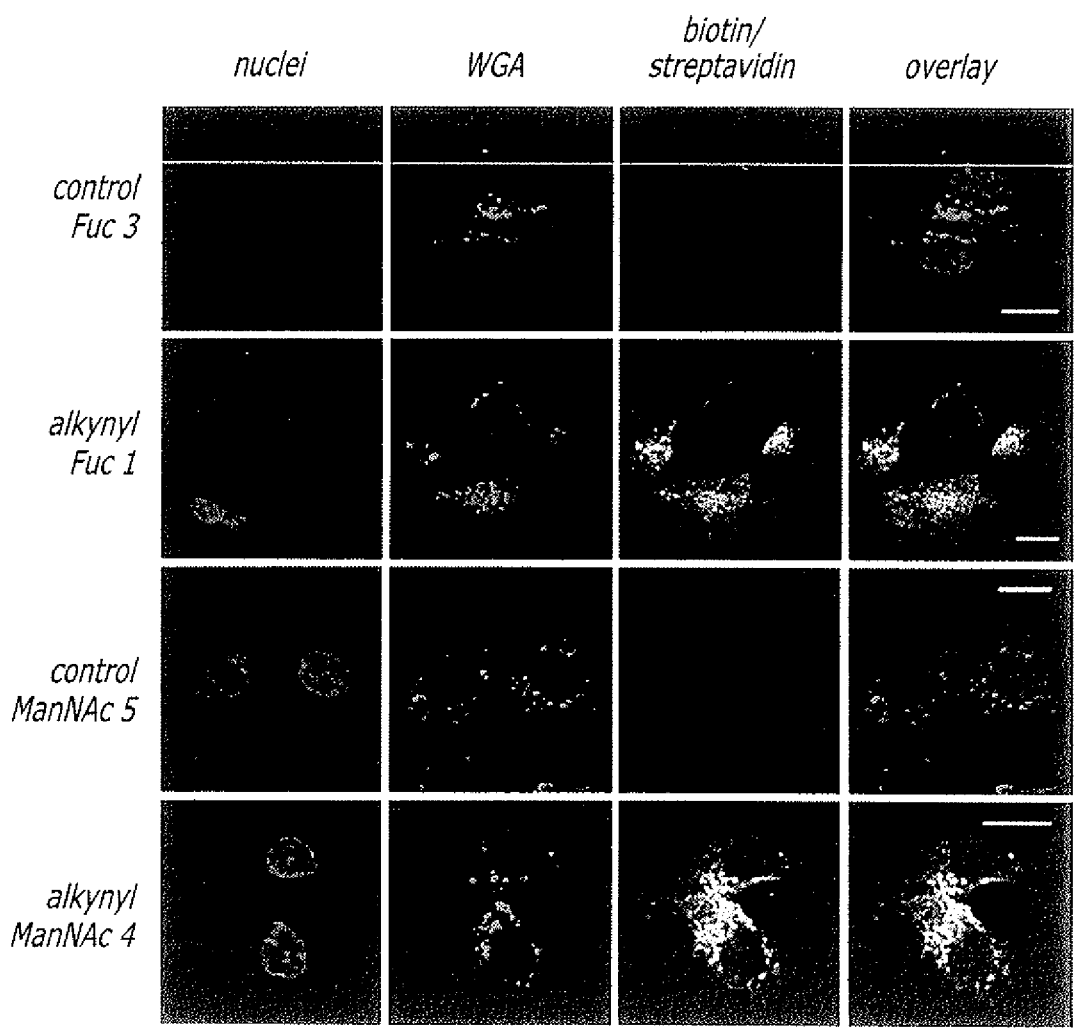
FIG. 4 shows fluorescent imaging of fucosyl and sialyl glycoconjugates in cells. Confocal microscopy of Hep3B cells treated with 200 micromolar Fuc analogs or 25 micromolar ManNAc analogs. Cellular glycoconjugates were biotin-labeled and stained with streptavidin (fluorescein, green), WGA lectin (Alexa Fluor 594, red), and Hoechst 33342 (blue). (Scale bars: 20 micrometer).
Figure 5:
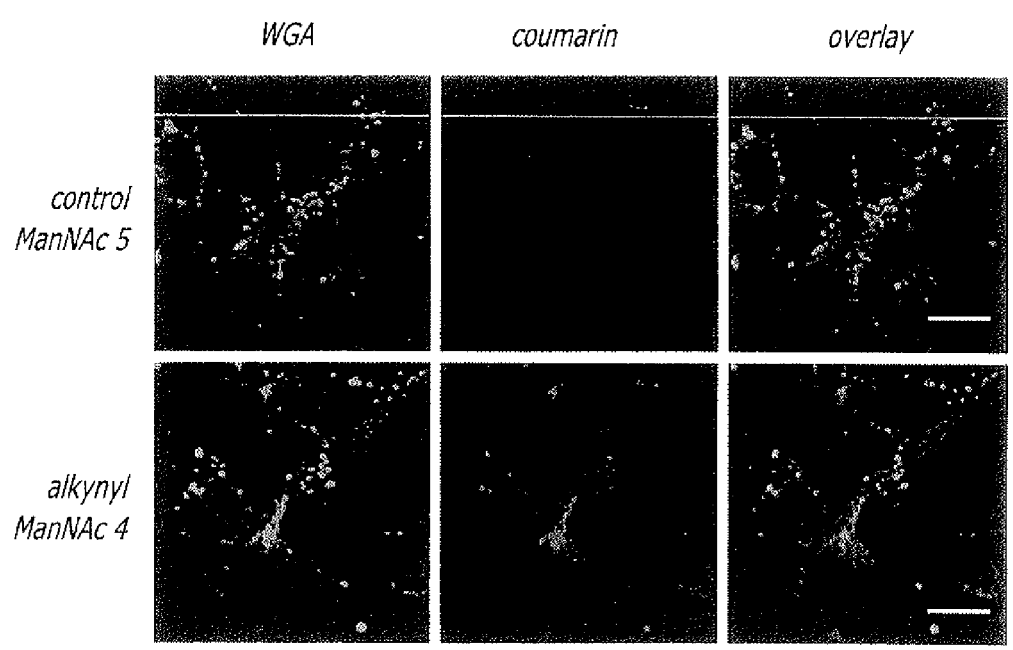
FIG. 5 shows visualization of derivatized alkynyl-tagged sialyl glycoconjugates in cells using "click-activated" fluorogenic labeling. 7. Shown is confocal microscopy of coumarin-labeled Hep3B cells. Cells were treated with 25 micromolar derivatized ManNAc 5 or 4 for 3 days, and then labeled with fluorogenic coumarin probe 7 (blue) and stained with WGA lectin (Alexa Fluor 594, red). (Scale bars: 20 micrometer).
Figure 10A:
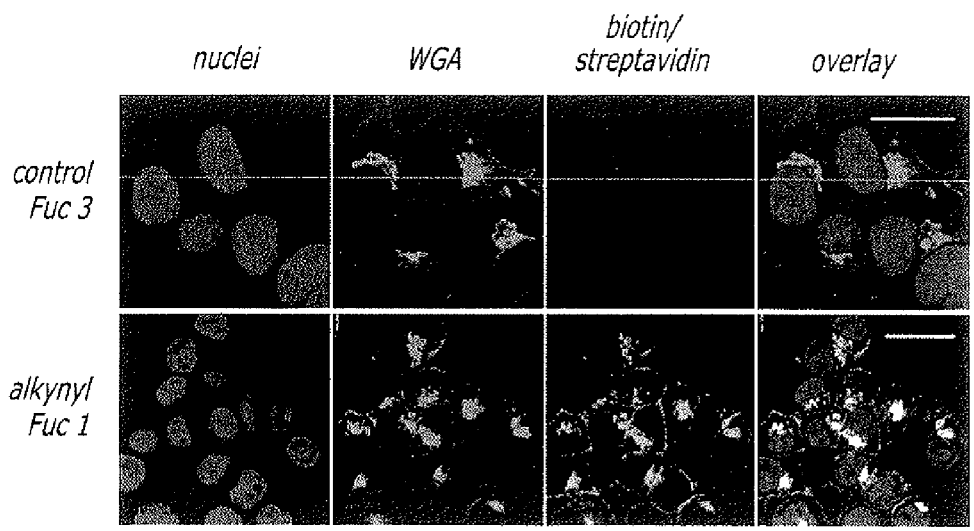
FIG. 10 shows fluorescent imaging of fucosyl and sialyl glycoconjugates in cells. Confocal microscopy of MCF-7 breast cancer cells treated with 200 micromolar derivatized Fuc analogs (A) or 25 micromolar derivatized ManNAc analogs (B). Cells were biotin-labeled and stained with streptavidin (fluorescein; green), WGA lectin (Alexa Fluor 594; red), and Hoechst 33342 (blue). Scale bars represent 20 micrometers.
Figure 10B:
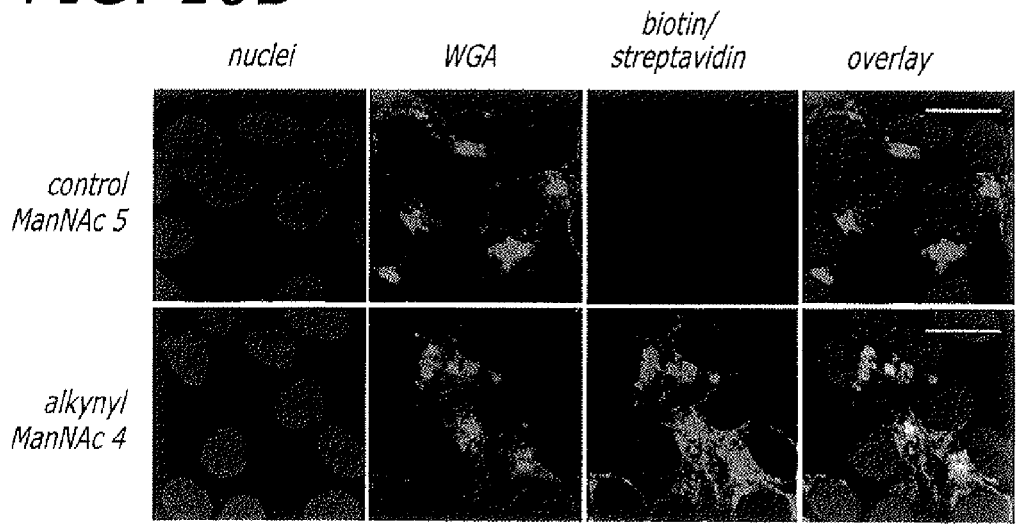

One exemplary implementation of the disclosure provides a method to visualize the localization of glycoconjugates using alkynyl sugar tagging. To visualize the localization of glycoconjugates tagged with alkynyl sugars, adherent cells are grown on slides in the presence or absence of derivatized alkynyl sugars. After a 3-day-incubation, cells attached to the slides are fixed, permeabilized, and labeled with either biotin probe 6 or fluorogenic probe 7 for fluorescent signal analysis with confocal microscopy (FIGS. 4, 5, 10 and 11). For comparison, samples are also stained with wheat germ agglutinin (WGA, a Golgi marker) and Hoechst 33342 (marker for cell nuclei). In one aspect of the method, cancer cell lines, such as Hep3B (hepatocellular carcinoma) and MCF-7 (breast adenocarcinoma) cells, are treated with derivatized alkynyl Fuc 1 to result in a strong punctate-labeling signal after labeling tagged glycoconjugates with a biotin probe 6 and staining with fluorescein-conjugated streptavidin. This signal shows significant overlap with the WGA signal, indicating the labeled fucosyl glycoconjugates are localized in Golgi apparatus (FIGS. 4 and 10). Similar results are obtained from cells treated with alkynyl ManNAc 4, which probes for tagged sialic acid-containing glycoconjugates, when labeled by biotin probe 6 and fluorogenic probe 7 (FIGS. 4, 5, 10 and 11). Consistent with the results from flow cytometry, confocal microscopic analysis of cells treated with control sugars 3 and 5 gives very low background after reacting with click probes, confirming the labeling of alkynyl containing glycoconjugates is specific and sensitive.

Labeling of Glycoconjugates in Cell Extract.

Figure 6A:
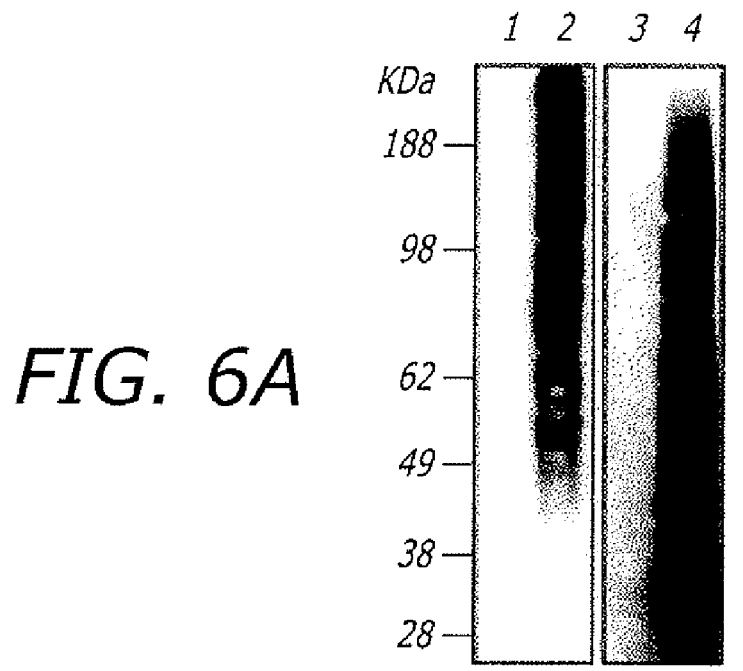
FIG. 6 shows detection of derivatized alkynyl-tagged glycoconjugates in cell extracts subjected to Western blot. Glycoconjugates tagged with derivatized alkynyl sugars were labeled and subsequently detected by immunoblotting of biotin tag (A) or fluorescent imaging of fluorogenic coumarin probe 7 (B). Protein extracts from cells grown with different sugars were analyzed (lane 1, control Fuc 3; lane 2, alkynyl-derivatized Fuc 1; lane 3, control ManNAc 5; lane 4, alkynyl-derivatized ManNAc 4). The protein gel (4-12%) was subsequently stained by Coomassie blue after fluorescent imaging, to verify equal protein loading.
Figure 6B:
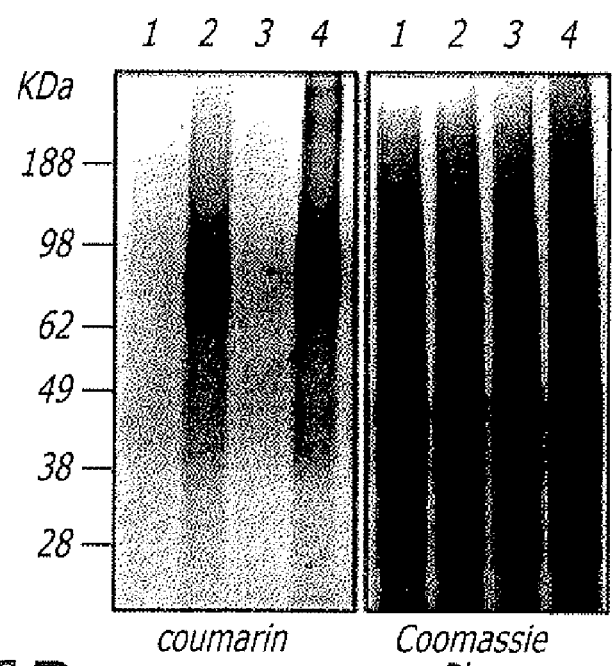
Figure 11:
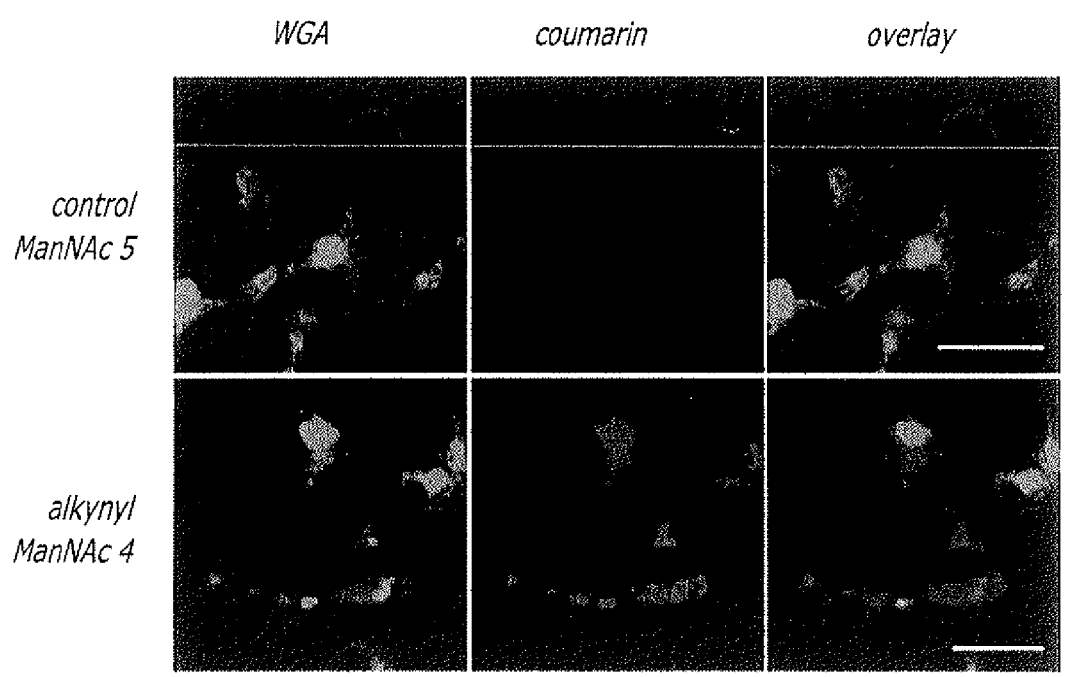
FIG. 11 shows visualization of tagged sialyl glycoconjugates in cells using labeling via click-activated probe 7: confocal microscopy of coumarin-labeled MCF-7 cells. Cells were treated with 25 micromolar ManNAc analogs 5 or 4, and then labeled with fluorogenic coumarin probe 7 (blue) and stained with WGA lectin (Alexa Fluor 594; red). Scale bars represent 20 micrometers.
Figure 12:
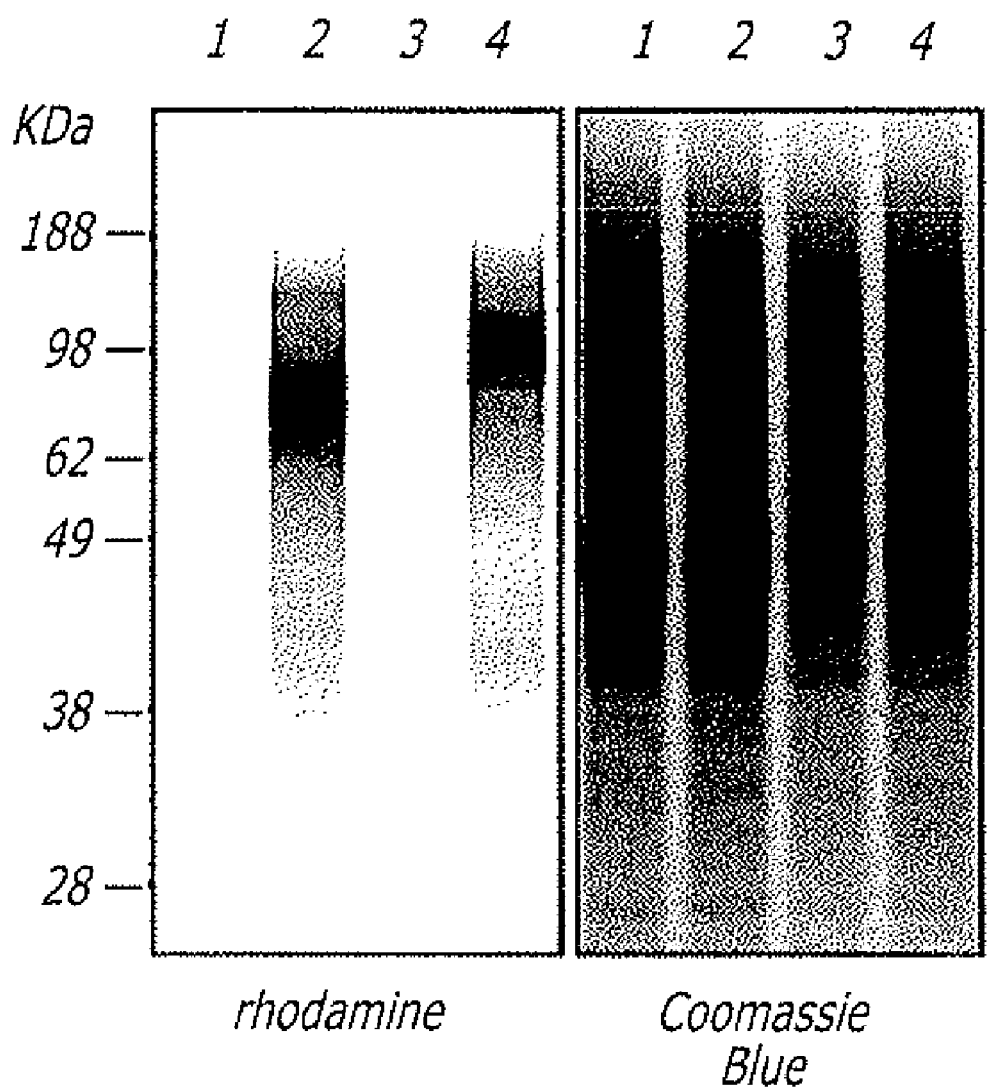
FIG. 12 shows detection of alkynyl-tagged glycoconjugates in cell extracts. Glycoconjugates tagged with alkynyl-derivatized sugars were labeled and detected by azido rhodamine probe. Protein extracts from cells grown with different sugars were analyzed by SDS-PAGE (12% gel), fluorescent imaging, and Coomassie Blue stain (lane 1: control Fuc 3; lane 2: alkynyl Fuc 1; lane 3: control ManNAc 5; lane 4: alkynyl ManNAc 4).

Because the herein disclosed labeling system enables the identification of cellular glycoconjugates, it can also serve well in glyco-proteomic applications aimed at discovering unknown glycosylated targets for diagnostic and therapeutic purposes. In one aspect of the disclosure, cell extracts are analyzed after growing cells in a medium containing alkynyl-derivatized sugars to demonstrate the detection of individual labeled proteins. Soluble lysate fractions are labeled with biotin probe 6, fluorogenic probe 7, or a standard azido-derivatized rhodamine probe used in proteomics before separating proteins by SDS/PAGE. As shown in FIG. 6A, specific biotin-labeling signals were detected by Western blot in proteins from cells treated with alkynyl sugars 1 and 4. Positive fluorescent signal was also detected in alkynyl positive protein lysate when labeled with fluorogenic 3-azido-7-hydroxycoumarin 7 and rhodamine probes (FIG. 6B and FIG. 11). Proteins harvested from cells grown with control sugars 3 and 5 and processed utilizing the same cycloaddition labeling process, showed little to no signal by Western blot or fluorescence. The labeling patterns for Fucyne and ManNAcyne are notably different, indicating the detection of unique glycoconjugates. The data herein presented demonstrate the feasibility and utility of labeling and identifying individual glycoconjugates by using this probing system. Moreover, further processing, including a streptavidin/avidin enrichment or gel slice purification, will allow for comparative identification by proteomic mass spectrometry techniques of unknown glycoconjugates expressed at different cell status, for instance, un-differentiated verses differentiated cells, or normal verses cancer cells.

The ability to visualize and isolate cellular glycoconjugates is useful to deconvolute the complexity and microheterogeneity that make it difficult to study their biological function. Toward this goal, several metabolic oligosaccharide engineering techniques have been developed, wherein the endogenous biosynthetic machinery for glycosylation is exploited to insert sugar analogs in place of their native counterparts. The tagged glycoconjugates, which contain bioorthogonal chemical handles, can then be chemoselectively labeled with a complementary reactive probe for further manipulation, including visualization or isolation. Recently, we designed a system for incorporating derivatized 6-azido derivatized Fuc analogs as cellular glycoconjugate "tags" with subsequent labeling with alkynyl-derivatized probes using CuAAC. We also introduced the use of this process for selective and specific labeling of modified glycoconjugates at the cell surface as well as in intracellular environments. Here, we have expanded the scope of our specific glycoconjugate tagging system by establishing that another useful chemical reporter, the alkyne group, can also be used to "tag" cellular glycoconjugates when appended on Fuc and ManNAc derivatives. Similar to its azide counterpart, the alkyne is a small, inert, bioorthogonal group that can be chemoselectively labeled by using click chemistry. The presently disclosed alkynyl Fuc and ManNAc saccharides represent a robust platform for labeling fucosylated and sialylated glycoconjugates in vivo. Formerly, azide sugar analogs were incorporated into glycoconjugates. However, it has been found that the azido Fuc analog is quite toxic to cells at the levels required for efficient labeling, which might in turn lead to aberrant cellular glycan profiles. The alkynyl Fuc, on the other hand, is much less toxic, yielding higher signals and less background, when cellular incorporation was monitored by flow cytometry. Alkynyl-derivatized ManNAc is not toxic at the low levels of the modified sugar required for efficient glycoconjugate labeling as observed by flow cytometry and microscopy. Without being bound by theory, this likely reflects the higher relative abundance of sialic acid verses Fuc residues. The alkynyl sugars also are efficient ligation partners for click activated fluorogenic and standard click probes. Tagging with click-activated probes is particularly useful because of the generation of an instant signal upon ligation with modified glycoconjugates that does not produce any significant background. As established by each of the herein described visualization methods (flow cytometry, confocal microscopy, and SDS/PAGE), the signal generated by the click-activated probe is equivalent to that of the biotin-secondary detection systems; however, it requires one less incubation step and no washing. Furthermore, the click-activated probes are small and hydrophobic, making them more amenable to intracellular penetration and tagging in living cells. The utility of this approach for probing interesting glycoconjugates was demonstrated by treating several human cancer cell lines with the alkynyl sugar substrates and subjecting them to several methods of analysis. In all cases, fluorescent-labeling of cell surface glycoconjugates is witnessed by flow cytometry. Information about intracellular glycoconjugate labeling and localization was determined by using confocal microscopy. Here, it is demonstrated that both alkynyl Fuc and ManNAc modified glycoconjugates are localized in the Golgi, consistent with their proposed site of transfer. Notably, detailed analysis of microscopy images can supply quantitative data within regions of colocalization, which may provide a useful tool for monitoring glycoconjugate levels and trafficking.

In another aspect, individual modified glycoconjugates can be separated and visualized by SDS/PAGE analysis, setting the stage for further proteomic analysis. In future studies, we plan to extend and combine these methodologies to obtain information about cellular glycoconjugates under different physiological disease states and cellular statuses, such as stress, apoptosis, or inflammation. Comparative studies between various stages of cancer progression, in addition to pulse-chased techniques to follow the dynamics of newly synthesized proteins within individual cellular systems should provide much needed snapshots of critical glycoconjugate behavior. Indeed, in preliminary studies with prostate cancer cells, we observed an increase in the fucosylated glycoconjugate signal when compared with noncancerous prostate controls (FIG. 10). This indicates that there might be some interesting correlations between increased Fuc expression and prostate cancer, a fact that is already well known for numerous cancers. Notably, it is important to consider that the introduction of modified sugars might change the cellular activity of certain glycoconjugates. Perturbations in glycoconjugate-mediated binding have been noted with viral receptors and lectin interactions in metabolic oligosaccharide engineering studies where sialic acid derivatives were introduced into cellular glycoconjugates. Accordingly, these studies also found that some Fuc lectins, including *aleuria aurantia* lectin (AAL; specific for alpha-1,6- or alpha-1,3-linked Fuc) and *Ulex Europaeus* Agglutinin I (UEA-1; specific for alpha-1,2-linked Fuc), bound with significantly lower avidity among cells treated with alkyne Fuc verses control (FIG. 11). These results are not surprising, considering that a change from a methyl to a more bulky alkynyl group may interfere with the recognition in the small conserved hydrophobic pocket found in many Fuc lectins. Indeed, in some cases, altered biological responses may prove useful for perturbing and profiling the function of unknown carbohydrate binding proteins. On the other hand, some glycoconjugate modifications do not seem to greatly affect binding interactions, past studies analyzing the binding of selectins to synthetic analogues of sialyl Lewis x showed a significant tolerance for N-acyl modification on sialic acid. Thus, the analysis of cells treated with modified sugars over an extended period must be evaluated carefully. To circumvent any artifacts from altered activity or differential cellular uptake, pulse-chase experiments may be useful. These experiments would result in lower levels of modified glycoconjugates, while presenting a comparable cell-to-cell snap shot of glycoconjugate behavior.

The usage of alkynyl sugars is further applied to analyze tagged glycoproteomes through metabolic oligosaccharide engineering (MOE) in *Helicobacter pylori* (*H. pylori*). Although rare among prokaryotes, Gram-negative bacterium *H. pylori* possesses the glycosylation machinery necessary to fucosylate its glycoconjugates. This fucosylation process can produce Lewis antigens, among other structures, on glycoconjugates and enables *H. pylori* to bind to host cells and subsequently evade the host immune system, thus contributing to persistent infection in stomach. MOE strategy provides the opportunity to study fucosylated glycoconjugates of clinical *H. pylori* isolates from various stages of infection, so that the link between fucosylation and the development of gastric ulcer and cancer.

Figures 13A, 13B:
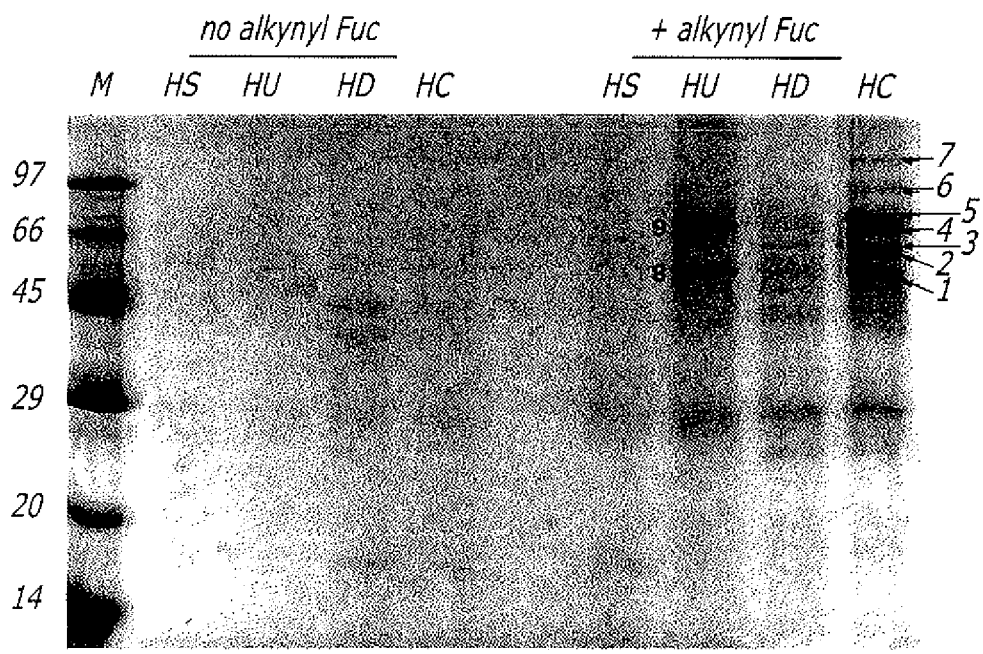
FIG. 13 shows SDS-gel based derivatized fucosylated glycoproteomic profiling of *H. pylori*. (A) Affinity purification of derivatized alkynyl-tagged fucosylated proteins in various *H. pylori* strains after labeling with biotin probe. HS: gastric strain. HU: gastric ulcer strain. HD: duodenal ulcer strain. HC: gastric cancer strain. (B) Protein identified from different strains of *H. pylori* by tagging with derivatized alkynyl Fuc and further labeling and subsequent visualization and isolation of tagged glycoconjugates.

Representative *H. pylori* strains isolated from human gastric biopsy specimens, including gastritis (HS), duodenal ulcer (HD), gastric ulcer (HU) and gastric cancer (HC), were subjected to MOE: all the strains were grown on CDC agar plate supplemented with 200 micromolar derivatized alkynyl Fuc 1 for two days under micro-aerobic atmosphere (5% $O_2$, 15% $CO_2$, 80% $N_2$). Tagged protein extracts were prepared in lysis buffer (1% NP-40, 150 mM NaCl, 100 mM sodium phosphate pH7.5, 1×EDTA-free protease inhibitor cocktail) and subjected to subsequent labeling with biotin probe 6 (protein 1 mg/ml with 0.1 mM azido biotin 6/0.1 mM Tris-triazoleamine catalyst/1 mM $CuSO_4$/2 mM sodium ascorbate in lysis buffer) at room temperature for 1 h. To isolate glycoproteins, 1 mg labeled protein samples were precipitated with 10% TCA for 30 min to remove excessive biotin probe, re-dissolved in 1 ml of 0.2% SDS/PBS, and immunoprecipitated with 50 □l anti-biotin agarose beads (Vector Laboratories) at room temperature for 1 h. Immunoprecipitates were then analyzed by SDS-PAGE and stained for visualization. As shown in FIG. 13A, several proteins were detected in MOE-tagged *H. pylori*, while no proteins were isolated from non-tagged *H. pylori* proteome samples, indicating that the immunoprecipitation process was specific. Notably, more fucosyl proteins were detected in HC and HU strains, and fewer proteins were observed in HS and HD strains. Protein bands revealed in SDS-protein gel (marked with numbers in FIG. 13A) were excised, extracted, reduced, alkylated, tryptic digested to elute peptides and subjected to LC-MS$^2$ analysis for protein identification (FIG. 13B).

Figure 14:
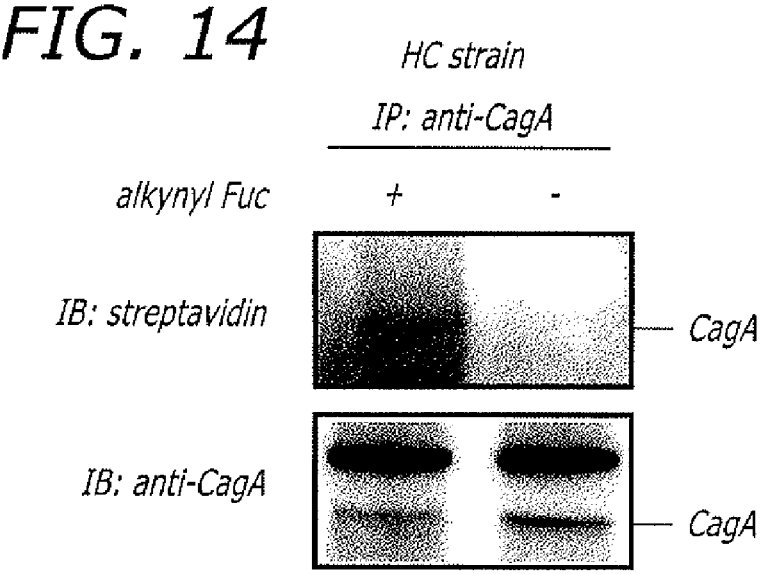
FIG. 14 shows examination of derivatized alkynyl-tagged fucosylated glycoconjugates on CagA in *H. pylori* cancer strain by immunoprecipitation and immunoblotting.

To validate the fucosylation of proteins in *H. pylori*, we examined CagA (cytotoxicity-associated immunodominant antigen), a virulence factor reported to associate with malignancy, for the incorporation of alkynyl Fuc 1 by anti-CagA antibody in HC strain as follows: Labeled proteins extracted from control or alkynyl Fuc 1-treated HC samples were subsequently labeled via-cycloaddition with biotin probe, followed by immunoprecipitation with anti-CagA antibody. The biotinylated Fuc tags present on CagA protein were revealed by peroxidase-conjugated streptavidin on protein blot. By comparison with the CagA protein isolated from a control sample (derived from cells grown without alkynyl Fuc 1), a specific signal is only detected in MOE-tagged HC strain, indicating the existence of alkynyl Fuc tags on CagA protein (FIG. 14).

Secretory glycoconjugates are known to be continuously recycled. Glycoconjugates are synthesized in the ER/Golgi, and then exported to subcellular locations, primarily the cell-surface, before being endocytosed to the lysome, where they are processed and ultimately taken back to the Golgi to start the cycle again. At this point, the kinetics of these processes are not well understood, and conflicting reports exist. Pulse-chased experiments can be used examine trafficking of glycans, and to monitor the differential trafficking of glycans in cells at different stages of disease. It is worth noting, that by pulsing the sugars cellular perturbations caused by the modified architecture of the akynylated glycans and/or toxicity of the azido-fucose derivative may be reduced by use of lower concentrations and time exposure to derivatized sugars.

Figure 15:
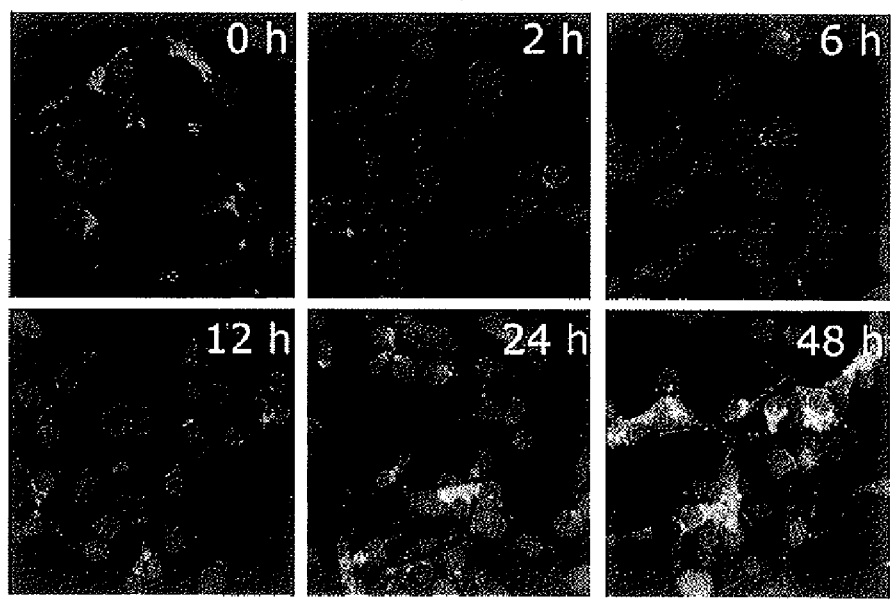
FIG. 15 shows time-lapse microscopy of pulse-chased Hep3b cells grown for 30 minutes in medium containing Fucyne, with tagged glycoconjugate structures subsequently labeled with biotin and detected using streptavidin-FITC as a secondary label at 2 hour intervals after completion of the Fucyne pulse. Additional cellular structures are visualized using alternative labeling systems (e.g., WGA lectin used to visualize Golgi apparatus, and Hoechst used to visualize nucleus).

Pulse-chased MOE experiments entail growing cells of interest to log-phase levels and then exposing them to the sugar analogs in the growth medium, as prescribed by standard MOE, but only for a 30 minute pulse, before replenishing with fresh medium devoid of sugars. Post sugar-pulse, the cells are grown for various lengths of time before analysis. FIG. 15 shows microscopy of Hep3B cells subjected to pulse-chase conditions with Fucyne, CuAAC labeled with biotin, and detected by streptavidin-FITC. The signal for the fucosylated glycans (green) may emerge as a co-localized yellow signal as early as 2 h, indicating significant overlap with the Golgi marker (red). A pure green signal may increase over longer periods following the Fucyne pulse, indicating a progression from the golgi to the cell surface (data that may be obtained for sialylated alkynyl glycans shows a similar trend). Notably, this progression from Golgi to cell surface using copper free click-reactions, label cell-surface glycans.

For example, by coupling the pulse-chase procedure with cellular markers of interest (e.g., to image the lysome with LysoTrackerRed, the Golgi with BODIPY ceramide TR, the endsome with Alexafluor-labeled transferrin, or the ER with R6-rhodamine B hexyl-ester chloride) information may be obtained about dynamics and trafficking of glycans in cancer cells. Using orthogonal sugar probes, for instance FucAz and ManNAcyne (or Fucyne and azido sialic acid derivatives), in combination with probe fluorophores that emit at different wavelengths, may allow for simultaneous labeling and imaging of both sugars in the same sample. A combination of copper-free and CuAAC may also provide more in-depth information about cellular trafficking. Pulsing Fucyne and then azido-derivatized sugars may provide more information about spatial and temporal trafficking of fucosylated glycoconjugates (First pulse at the cell surface, while second pulse is in ER, etc). Finally, Double labeling with FucAz and ManNAcyne may be used to monitor the trafficking of fucosylated verses sialylated glycans, this data may be further used to quantify, contrast and compare the relative numbers of fucosylated verses sialylated verses fucosylated and sialylated glycans found at a cell in various life cycle stages.

In one exemplary implementation of the disclosure, an Intermediary of Azido Derivatized Fucose is 6,7-Deoxy-1,2:3,4-di-O-isopropylidene-☐-L-galacto-hept-6-ynopyranoside A suspension of PCC (1.3 g, 6.0 mmol), NaOAc (1.0 g, 12.0 mmol) and 4 Å molecular sieves (2.7 g) in dry $CH_2Cl_2$ (18 mL) was stirred for 1 h. To this mixture was added a solution of 17 (520 mg, 2.0 mmol) in dry $CH_2Cl_2$ (9 mL) dropwise, and the mixture was stirred at room temperature for 2 h. The reaction mixture was diluted with hexane/ether (1:1, 50 mL), and the solution was filtered through a bed of silica gel. The filtrate was concentrated to give the crude aldehyde. To a suspension of tBuOK (471 mg, 4.2 mmol) in dry THF (5 mL) was added a solution of $(EtO)_2P(O)CHN_2$ (748 mg, 4.2 mmol) in THF (5 mL) at −78° C. and the mixture was stirred at 5 min under $N_2$ gas. To this solution, a solution of the aldehyde in THF (5 mL) was added, and the mixture was allowed to warm to room temperature and continued to stir overnight. The reaction mixture was quenched with 100 mL of water, and the mixture was extracted with $CH_2Cl_2$. The extracts were washed with brine, dried over with $Na_2SO_4$, and evaporated. The residue was purified by flash column chromatography on silica gel (AcOEt/hexane 1:5) to afford 4 as a colorless oil (295 mg, 62%).

In conclusion, herein disclosed is a method for metabolic oligosaccharide engineering that can incorporate alkyne-bearing sugar analogs in cellular glycoconjugates. The utility of the alkynyl system has been demonstrated by incorporating Fuc and ManNAc derivative sugars into cancer cell lines, where they were visualized at the cell surface, intracellularly, and as individual glycoconjugates. The alkynyl Fuc sugar was also incorporated into fucoysylated cellular glycans produced by *H. pylori*, a causative agent of gastric cancer. Sugars were selected that report on Fuc (alkynyl Fuc) and sialic acid (alkynyl ManNAc) because these residues, in particular, have been linked to many aberrant glycoconjugates in cancer. Although several glycan epitopes binding sialic acid and fucose are known, there are likely many other as yet unidentified glycoconjugates and glycan activities that contribute. Identification of these glycan-related biomarkers and targets for therapeutic intervention is one of the key objectives in our strategy.

EXAMPLES

All chemicals were purchased as reagent grade and used without further purification. Reactions were monitored with analytical thin-layer chromatography (TLC) on silica gel 60 F254 plates and visualized under UV (254 nm) and/or by staining with 5% sulfuric acid or acidic ceric ammonium molybdate. $^1$H- or $^{13}$C-NMR spectra were measured on a Bruker DRX-500 or DRX-600 using $CDCl_3$ or DMSO-d$^6$ as the solvent (1H, 500 or 600 MHz; $^{13}$C, 125 or 150 MHz). Chemical shifts (in ppm) were determined relative to either tetramethylsilane (0 ppm) or deuterated chloroform (77 ppm). Mass spectra were obtained by the analytical services of The Scripps Research Institute. Biotin-conjugated Aleuria Aurantia Lectin (AAL), fluorescein-conjugated streptavidin, and fluorescein conjugated *Ulex Europaeus* Agglutinin I (UEA-1) was purchased from Vector laboratories (Burlingame, Calif.). RPMI 1640, DMEM, Alexa Fluor® 594-conjugated WGA lectin, and Hoechst 33342 were purchased from Invitrogen (Carlsbad, Calif.).

SuperBlock® Blocking buffer, peroxidase-conjugated goat anti-mouse IgG, and

SuperSignal® Chemiluminescent Substrate were obtained from Pierce (Rockford, Ill.).

EDTA-free protease inhibitor cocktail and anti-biotin MAb were purchased from Roche Applied Science (Indianapolis, Ind.).

Example 1

Synthesis of 1,2,3,4-tetraacetyl alkynyl fucose (Fuc) (1, mixture of anomers; Scheme 2)

To a flask containing compound 8 (0.05 g, 0.2 mmol), TFA solution (1 ml, 90% TFA in $H_2O$) was slowly added at 0° C.

Figure 7:
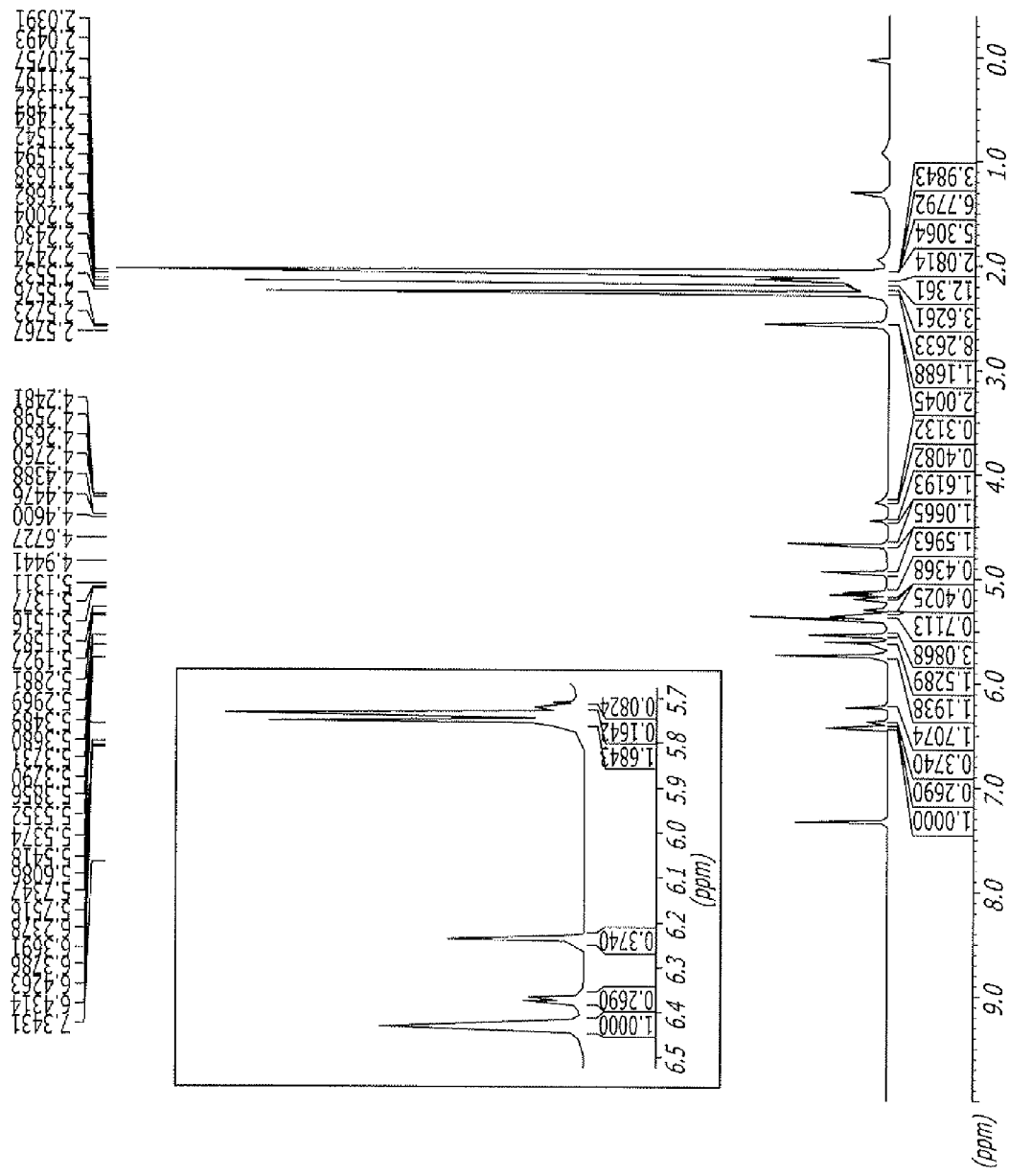
FIG. 7 shows $^1$H-NMR spectra of peracetylated alkynyl Fuc 1.
Figure 8:
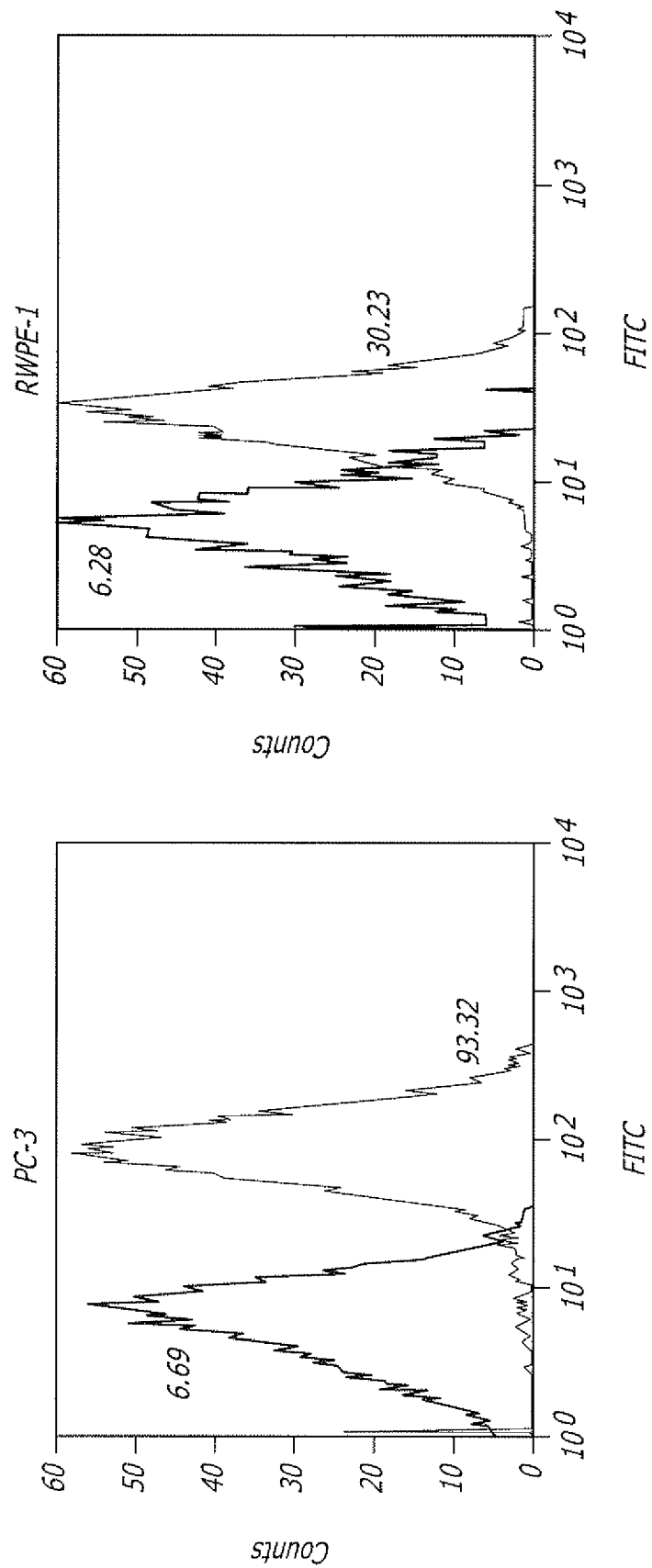
FIG. 8 shows tagging of fucosyl glycans with derivatized alkynyl sugars on prostate cancer PC-3 and RWPE-1 prostate cells. Cells were treated with alkynyl-derivatized Fuc analog 1 or 3, labeled with azido-biotin probe 6, and subjected to flow cytometry analysis. Filled histograms: cells treated with control Fuc 3; open histograms: cells treated with alkynyl-derivatized Fuc 1. Mean fluorescence intensity (MFI) of each peak is indicated.
Figure 9A:
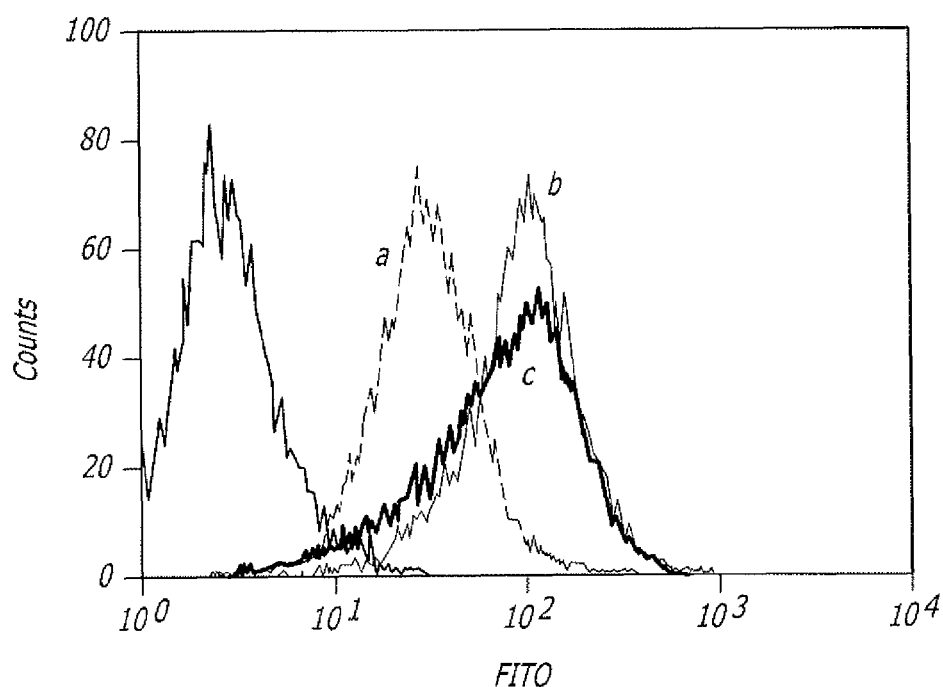
FIG. 9 shows lectin staining of alkynyl-derivatized Fuc 1-tagged PC-3 prostate cancer cells. Cells were treated with 200 micromolar derivatized alkynyl-derivatized Fuc 1, or Fuc 3, or left untreated. After three days, cells were labeled with biotin-conjugated AAL/fluorescein-conjugated streptavidin (A) or fluorescein-conjugated UEA-I (B). Fluorescent signal was detected by flow cytometry. AAL was used to detect □-1,6- or □-1,3-linked Fuc; UEA-I was used to detect □-1, 2-linked Fuc. Filled histogram: untreated cells without lectin stain; open histogram c: untreated cells stained with lectin; open histogram b: control Fuc 3-treated cells stained with lectin; open histogram a: alkynyl-derivatized Fuc 1-treated cells stained with lectin. AAL, *Aleuria Aurantia* Lectin; UEA-1, *Ulex Europaeus* Agglutinin I.
Figure 9B:
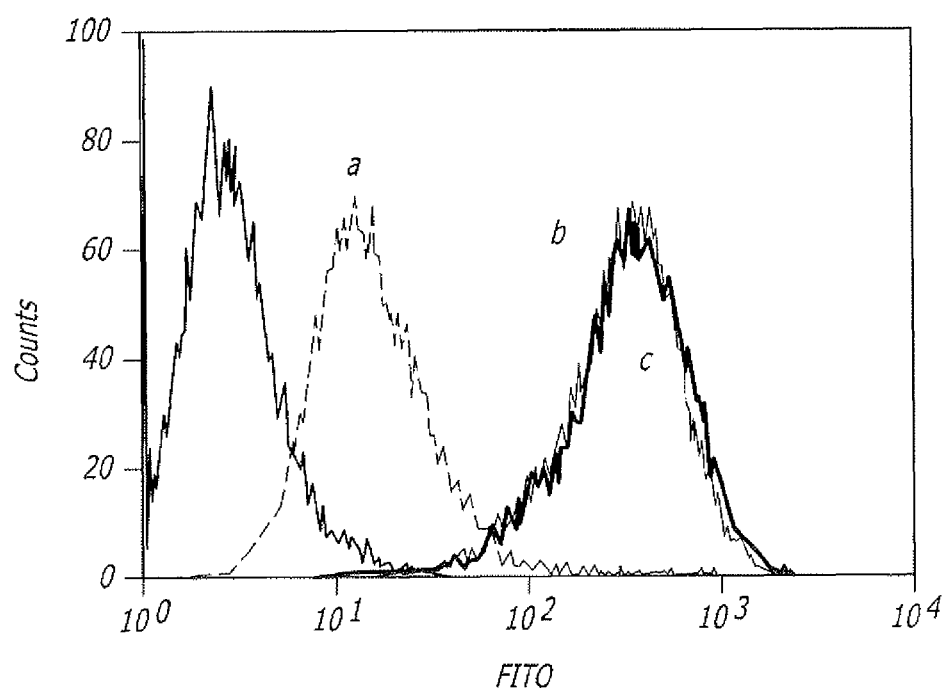

The reaction was stirred on ice for 1 h and concentrated in vacuo. The resulting residue was treated with pyridine (1 ml), N,Ndimethylaminopyridine (2.0 mg), and acetic anhydride (1 ml), stirred overnight, concentrated, and diluted with dichloromethane. This solution was then sequentially washed with 1 N aqueous HCl, saturated aqueous NaHCO$_3$, and brine. The organic phase was dried over anhydrous Na$_2$CO$_3$ and concentrated. Silica gel chromatography gave product 1 (0.055 g, 80%, □-pyranoside:β-pyranoside: □-furanoside:β-furanisude=30:51:11:8) as a colorless gum (FIG. 7). Partial $^1$H-NMR of mixture (500 MHz, CDCl$_3$) □ 5.74 (d, J=8.4 Hz, H-1 (βpyr)), 6.24 (s, H-1 (□fur)), 6.36 (d, J=4.8 Hz, H-1 (βfur)), 6.43 (d, J=2.6 Hz, H-1 (□pyr)); ESI-TOF-HRMS m/e calculated for (M+Na)$^+$ C$_{15}$H$_{18}$O$_9$Na 365.0843; found 365.0839.

Example 2

Synthesis of N-4-pentynoylmannosamine (10, mixture of anomers; Scheme 3)

A mixture of D-mannosamine hydrochloride (863 mg, 4.0 mmol), N-succinimidyl 4-pentynoate 9 (781 mg, 4.0 mmol), triethylamine (1.67 ml, 12.0 mmol) in DMF (31 ml) was stirred at room temperature overnight. The reaction mixture was concentrated in vacuo, and the residue was purified by flash column chromatography (CHCl$_3$/MeOH 8:1) to give N-4-Pentynoylmannosamine, 10 (898 mg, 87%); $^1$H-NMR (500 MHz, D$_2$O) □2.37 (t, 2.63H, J=2.5 Hz), 2.48-2.63 (m, 10.5H), 3.38-3.42 (m, 1H), 3.52 (t, 1H, J=10 Hz), 3.63 (t, 1.63H, J=10 Hz), 3.69-3.91 (m, 7.89H), 4.05 (dd, 1.63H, J=4.5 and 10 Hz), 4.35 (dd, 1.63H, J=1.5 and 4.5 Hz), 4.47 (dd, 1H, J=1.5 and 4.5 Hz), 5.03 (d, 1H, J=1.5 Hz), 5.13 (d, 1.63H, J=1.5 Hz); $^{13}$C-NMR (125 MHz, D$_2$O)□ 14.78, 14.91, 34.62, 34.79, 53.67, 54.50, 60.91, 60.93, 67.01, 67.28, 69.25, 70.56, 70.71, 72.47, 72.50, 76.80, 84.04, 84.45, 93.36, 93.67, 175.68, 176.41; ESI-TOF-HRMS m/e calculated for (M+H)$^+$ C$_{11}$H$_{17}$NO$_6$ 260.1129; found 260.1120.

Example 3

Synthesis of 1,3,4,6-tetra-O-acetyl-N-4-pentynoylmannosamine (4, mixture of anomers; Scheme 3)

A mixture of 10 (123 mg, 0.500 mmol) and acetic anhydride (0.227 ml, 2.40 mmol) in pyridine (4 ml) was stirred at room temperature overnight. The reaction mixture was concentrated in vacuo, and the residue was dissolved in CH$_2$Cl$_2$ and washed with water. The organic layer was dried over Na$_2$SO$_4$ and evaporated. The residue was purified by flash column chromatography (AcOEt/Hexane 1:4) to give 1,3,4,6-tetra-O-acetyl-N-4-pentynoylmannosamine, 4 (183 mg, 86%); $^1$H-NMR (500 MHz, CDCl$_3$) □ 2.00 (s, 9H), 2.06 (s, 9H), 2.097 (s, 3H), 2.10 (s, 3H), 2.11 (s, 3H), 2.14-2.18 (m, 3H), 2.19 (s, 6H), 2.46-2.58 (m, 12H), 3.81-3.87 (m, 1H), 4.00-4.15 (m, 5H), 4.23-4.30 (m, 3H), 4.69 (dd, 2H, J=4.5 and 10 Hz), 4.82 (dd, 1H, J=4.5 and 10 Hz), 5.09 (dd, 1H, J=4.5 and 10 Hz), 5.17 (t, 1H, J=10 Hz), 5.23 (t, 2H, J=10 Hz), 5.33 (dd, 2H, J=4.5 and 10 Hz), 5.90 (s, 1H), 6.03 (s, 2H), 6.36 (d, 1H, J=9.5 Hz), 6.54 (d, 2H, J=9.5 Hz); $^{13}$C-NMR (125 MHz, CDCl$_3$) □ 15.29, 15.40, 20.99, 21.01, 21.06, 21.09, 21.15, 21.21, 35.51, 35.72, 35.86, 49.80, 62.55, 62.70, 65.87, 66.07, 69.25, 70.39, 70.54, 70.63, 71.63, 73.69, 83.07, 83.11, 90.98, 92.08, 168.59, 168.81, 170.07, 170.44, 170.51, 170.98, 171.82, 172.15; ESI-TOF-HRMS m/e calculated for (M+H)$^+$ C$_{19}$H$_{25}$NO$_{10}$ 428.1551; found 428.1549.

Example 4

Synthesis of 3-azidopropyl biotin amide (6; Scheme 4)

A mixture of D-(+)-biotin (100 mg, 0.41 mmol), 1-azido-3-aminopropane (82 mg, 0.82 mmol) O-(benzotriazol-1-yl)-N,N,N',N'-tetramethyluronium hexafluorophosphate (311 mg, 0.82 mmol) and N,N-diisopropylethylamine (106 mg, 0.82 mmol) in DMF (5 ml) was stirred at room temperature for 2 h. The reaction mixture was concentrated in vacuo, and the residue was purified by flash column chromatography (CHCl$_3$/MeOH 10:1) to give the amide 6 (53 mg, 40%); $^1$H-NMR (400 MHz, DMSO-d$^6$) □ 1.21-1.35 (m, 4H), 1.45-1.55 (m, 3H), 1.60-1.67 (m, 3H), 2.05 (t, 2H, J=7.6 Hz), 2.57 (d, 1H, J=12.6 Hz), 2.82 (dd, 1H, J=4.8 and 12.6 Hz), 3.07-3.10 (m, 3H), 4.10-4.14 (m, 1H), 4.28-4.32 (m, 1H), 6.36 (s, 1H), 6.42 (s, 1H), 7.84 (m, 1H); ESI-TOF-HRMS m/e calculated for (M+H)$^+$ C$_{13}$H$_{23}$N$_6$O$_2$S 327.1598; found 327.1598.

Example 5

Flow Cytometric Analysis of Fluorescent Labeling on PC-3 Cell Surface

PC-3 cells were grown in RPMI 1640 (Invitrogen) supplemented with 10% FCS and peracetylated alkynyl Fuc 1 or control Fuc 3 for 3 days at 37° C. Cells were then harvested, washed with 1% FCS/PBS, resuspended (5×105 cells) in 100 µl of staining solution (1 µg/ml lectin conjugates in 1% FCS/PBS). Cells were then incubated on ice for 30 min and washed twice with 1% FCS/PBS. Cells stained with biotin-conjugated AAL were subsequently stained with fluorescein-conjugated streptavidin (0.5 µg/sample in 50 µl of 1% FCS/PBS) for 30 min on ice, and washed three times with 1% FCS/PBS. Data were acquired by FACSCalibur, and were analyzed by CellQuestPro software (BD Biosciences).

Example 6

Flow Cytometric Analysis of Fluorescent Labeling on Jurkat Cell Surface

Jurkat cells were cultivated (2×10$^6$/10 ml) in RPMI medium 1640 supplemented with 10% FCS and various concentrations of peracetylated alkynyl sugars 1, 2, or 4 or native sugars 3 or 5, for 1-3 days at 37° C. Cells were then harvested, washed with 0.1% FCS/PBS, and resuspended (106 cells) in 100 microliters of click reaction solution (0.1 mM biotin probe 6 or fluorogenic probe 7/0.1 mM Tris-triazoleamine catalyst/0.1 mM CuSO$_4$/0.5 mM sodium ascorbate, in PBS). The reaction was incubated at room temperature for 30 min, and then the cells were washed twice with 0.1% FCS/PBS. Cells treated with biotin probe 6 were subsequently stained with fluorescein-conjugated streptavidin (0.5 microgram per sample in 50 microliters of 1% FCS/PBS) for 30 min at 4° C., and washed three times with 1% FCS/PBS. Data were acquired by BD LSR II with FACSDiva software, and were analyzed by CellQuestPro software (BD Biosciences). Detection of fluorescent adduct with probe 7 was monitored with a 408 nm laser and a 440/40 bandpass filter for excitation and emission, respectively.

Example 7

Microscopic Analysis of Fluorescent Labeling in Cells

Human hepatocellular carcinoma cells (Hep3B) or breast adenocarcinoma cells (MCF-7) were seeded onto six-well plates ($3\times10^5/2$ ml per well) containing glass coverslips, and were cultivated in 10% FCS/DMEM or 10% FCS/RPMI medium 1640. Growth medium was supplemented with a control sugar (200 micromolar Fuc 3 or 25 micromolar ManNAc 5 and an alkynyl-modified sugar (alkynyl Fuc 1 or alkynyl ManNAc 4 at the same concentration as control sugars). After growing for 3 days, cells on coverslips were fixed and permeabilized with acetone for 10 min, then subjected to the probe labeling reaction: 0.1 mM biotin probe 6 or fluorogenic probe 7/0.1 mM Tris-triazoleamine catalyst/1 mM $CuSO_4$/2 mM sodium ascorbate, in PBS, at room temperature for 30 min. Subsequently, the fixed and labeled cells were rinsed with PBS and stained with Alexa Fluor 594-conjugated WGA lectin (2 micrograms/ml in 5% BSA/PBS) and/or fluorescein-conjugated streptavidin (2 micrograms/ml in 5% BSA/PBS) at room temperature for 30 min. Hoechst 33342 (10 microgram/ml in PBS) was used to stain nuclei. Fluorescent images were captured by Bio-Rad (Carl Zeiss) Radiance 2100 Rainbow laser scanning confocal microscopy system.

Example 8

Labeling and Detection of Glycoconjugates in Cell Extracts

Cells were seeded at $3\times10^6/8$ ml per 10-cm dish and treated with control and test sugars (200 micromolar Fuc 3 vs. alkynyl derivatized Fuc 1, or 25 micromolar ManNAc 5 vs. alkynyl derivatized ManNAc 2) in growth medium at 37° C. After 3 days, cell extracts were prepared by resuspending the cells in 1 ml of lysis buffer (1% Nonidet P-40/150 mM NaCl/ protease inhibitor/100 mM sodium phosphate, pH 7.5). Protein extract (1 mg/ml) was labeled for 1 h at room temperature (conditions as outlined in microscopic analysis; the azido rhodamine probe was a gift from Benjamin F. Cravatt, The Scripps Research Institute). Labeled protein lysate was resolved by SDS/PAGE. For immunoblotting of biotin-labeled glycoconjugates, electrophoresed proteins were transferred onto PVDF membranes, blocked for 20 min with SuperBlock Blocking Buffer, probed for 1 h with anti-biotin MAb (1 microgram/ml), and incubated with peroxidase-conjugated goat anti-mouse IgG (1:7, 500 dilution) for 30 min. Each step was followed by a wash with 0.02% Tween 20/PBS (PBST). Signal was developed with SuperSignal Chemiluminescent Substrate and detected by exposure to x-ray film. For detecting the coumarin-labeled glycoconjugates, gels were examined under 365 nm UV light with a 535+/−50 nm filter. Images were taken by using a BioDoc-It imaging system (UVP). Rhodamine gels were analyzed.

Example 9

Labeling and Detection of Fucosylated Glycoconjugates in *H. pylori*

*H. pylori* isolated from clinical gastric specimens: gastritis (HS), duodenal ulcer (HD), gastric ulcer (HU) and gastric cancer (HC) were grown on CDC agar plate supplemented with 200 □M derivatized alkynyl Fuc 1 for two days under micro-aerobic atmosphere (5% $O_2$, 15% $CO_2$, 80% $N_2$).

Protein extracts were prepared in lysis buffer (1% NP-40, 150 mM NaCl, 100 mM sodium phosphate pH7.5, 1×EDTA-free protease inhibitor cocktail) and labeled with biotin probe 6 (protein 1 mg/ml with 0.1 mM azido biotin 6/0.1 mM Tris-triazoleamine catalyst/1 mM CuSO4/2 mM sodium ascorbate in lysis buffer) via cycloaddition at room temperature for 1 h. Labeled protein samples (1 mg) were then precipitated with 10% TCA for 30 min to remove excessive biotin probe, re-dissolved in 1 ml of 0.2% SDS/PBS, and immunoprecipitated with 50 microliter anti-biotin agarose beads (Vector Laboratories) at room temperature for 1 h. Immunoprecipitates were then analyzed by SDS-PAGE and stained for visualization. Protein bands were excised from SDS-gel, extracted, reduced, alkylated, tryptic digested to elute peptides and subjected to LC-MS/MS analysis for identifying peptide sequences in MS core in Genomics Research Center, Academia Sinica, Taipei, Taiwan.

Detection of CagA on protein blots: Protein extracted from control or alkynyl Fuc 1 analog-treated HC samples were subjected to cycloaddition labeling to label with biotin probe (protein 1 mg/ml with 0.1 mM azido biotin 6/0.1 mM Tris-triazoleamine catalyst/1 mM CuSO4/2 mM sodium ascorbate in lysis buffer), followed by immunoprecipitation with anti-CagA antibody (Santa Cruz). The derivatized alkynyl Fuc tags/biotin labeling on CagA protein were detected by peroxidase-conjugated streptavidin on protein blot.

Example 10

Pulse-Chase Analysis of Fucosylated and Sialylated Glycans

Cells of interest may be grown to log phase and then presented with various derivatized sugars for a limited period of time; for example, 30 minutes. After the limited period of time, the cells are no longer presented with the various sugars. The cells with glycoconjugates incorporating various tagged sugars may then be visualized over time through secondary detection/and or microscopy in relation to various intracellular and intercellular structures, in order to collect data on the trafficking and relative location of tagged and labeled glycoconjugates.

While various exemplary implementations of the present disclosure have been described in detail, it is apparent that modifications and adaptations of those exemplary implementations will occur to those skilled in the art. However, it is to be expressly understood that such modifications and adaptations are within the spirit and scope of the present disclosure.

We claim:
1. A method comprising:
    presenting an alkynyl-derivatized sugar to a cell,
    wherein the alkynyl-derivatized sugar has an alkynyl functional group, and wherein the cells is capable of producing a glycoconjugate; Incorporating the alkynyl-derivatized sugar into the cell,
    wherein the alkynyl-derivatized sugar is subsequently used by the cell to produce a tagged glycoconjugate;
    wherein the tagged glycoconjugate includes
    a glycan portion;
    a conjugate portion;
    and an alkynyl functional group; and
    reacting the tagged glycoconjugate with a probe to produce a labeled, tagged glycoconjugate.
2. The method of claim 1, further comprising:
    detecting the labeled glycoconjugate to determine the location of the labeled glycoconjugate in the cell.

3. The method of claim 1, further comprising:
    detecting the labeled glycoconjugate to determine the quantity of the labeled glycoconjugate in the cell.
4. The method of claim 1, further comprising:
    detecting the labeled glycoconjugate to determine the identity of the labeled glycoconjugate in the cell.
5. The method of claim 1 wherein the alkynyl-derivatized sugar is an alkynyl derivatized fucose.
6. The method of claim 1 wherein the alkynyl-derivatized sugar is an alkynyl derivatized fucose derivative.
7. The method of claim 1 wherein the alkynyl-derivatized sugar is 1,2,3,4-tetraacetyl alkynyl fucose or a 1,2,3,4-tetraacetyl alkynyl fucose derivative.
8. The method of claim 1 wherein the alkynyl-derivatized sugar is an alkynylderivatized N-acetylmannosine or an alkynyl-derivatized N-acetylmannosine derivative.
9. The method of claim 1 wherein the alkynyl-derivatized sugar is a sialic acid precursor.
10. The method of claim 1 wherein the alkynyl-derivatized sugar is 1,3,4,6-tetraO-acetyl-N-4-pentynoylmannosamine.
11. The method of claim 1 wherein the alkynyl-derivatized sugar is peracetylated.
12. The method of claim 1 wherein the alkynyl-derivatized sugar is acetylated.
13. The method of claim 1 wherein the alkynyl-derivatized sugar is ManNAcyne.
14. The method of claim 1 wherein the alkynyl-derivatized sugar is NeuAcyne.
15. The method of claim 1 wherein the alkynyl-derivatized sugar is Fucyne.
16. The method of claim 1 wherein the alkynyl-derivatized sugar is bioorthogonal.
17. The method of claim 1 wherein the alkynyl-derivatized sugar is subsequently incorporated into a glycoconjugate at a terminal position.
18. The method of claim 1 wherein the alkynyl-derivatized sugar is subsequently incorporated into a glycoprotein.
19. The method of claim 1 wherein the alkynyl-derivatized sugar is subsequently incorporated into a glycoprotein at a terminal position.
20. The method of claim 1 wherein the alkynyl-derivatized sugar is subsequently incorporated into a glycolipid.
21. The method of claim 1 wherein the alkynyl-derivatized sugar is subsequently incorporated into a glycolipid at a terminal position.
22. The method of claim 1 wherein the alkynyl-derivatized sugar is capable of fluorescence.
23. The method of claim 5 wherein the alkynyl-tagged glycoconjugate is a fucosylated glycoconjugate.
24. The method of claim 8 wherein the alkynyl-tagged glycoconjugate is a sialylated glycoconjugate.
25. The method of claim 1 wherein the probe is azido-derivatized.
26. The method of claim 1 wherein the probe reacts with the alkynyl-tagged glycoconjugate by azide-alkyne cycloaddition.
27. The method of claim 26 wherein the azide-alkyne cycloaddition reaction is copper (I) catalyzed.
28. The method of claim 26 wherein the probe- tagged glycoconjugate reaction generates a triazole moiety.
29. The method of claim 28 wherein the triazole moiety is generated while maintaining bioorthogonality of the functional groups.
30. The method of claim 28 wherein the triazole moiety is generated at biological pH.
31. The method of claim 28 wherein the triazole moiety is generated with nearly 100% reaction efficiency.
32. The method of claim 1 wherein the probe is fluorogenic and becomes fluorescent upon azide-alkyne cycloaddition reaction with the tagged glycoconjugate.
33. The method of claim 1 wherein the probe additionally comprises a biotin group.
34. The method of claim 11 wherein the probe additionally comprises a coumarin group.
35. The method of claim 34, wherein the coumarin probe is 3-azido-7-hydroxycoumarin.
36. The method of claim 2 wherein the detecting step comprises visualizing the location of labeled glycoconjugates by one or more techniques of flow cytometry and confocal microscopy.
37. The method of claim 2 wherein the detecting step comprises quantifying the labeled glycoconjugates by one or more techniques of flow cytometry, SDS-PAGE, Western blot, ELISA, confocal microscopy, and mass spectroscopy.
38. The method of claim 2 wherein the detecting step comprises identifying the labeled glycoconjugates by one or more techniques of flow cytometry, SDS-PAGE, Western blot, ELISA and confocal microscopy.
39. The method of claim 5 wherein the incorporating step further comprises growing the cell in the presence of from about 1 to about 1000 micromolar concentration of the alkynyl-derivatized fucose.
40. The method of claim 5 wherein the incorporating step comprises growing the cell in the presence of from about 50 to about 400 micromolar concentration of the alkynyl-derivatized fucose.
41. The method of claim 8 wherein the incorporating step comprises growing the cell in the presence of from about 1 to about 100 micromolar concentration of the alkynyl-derivatized N-acetylmannosamine.
42. The method of claim 8 wherein the incorporating step comprises growing the cell in the presence of from about 5 to about 50 micromolar concentration of the alkynyl-derivatized N-acetylmannosamine.
43. The method of claim 1 wherein the labeled glycoconjugate in the cell is on the surface of the cell.
44. The method of claim 1 further comprising treating the cell to permeabilize the cell prior to labeling.
45. A method comprising:
    presenting an alkynyl-derivatized sugar to a cell,
        wherein the alkynyl-derivatized sugar has an alkynyl functional group, and wherein the cell is capable of producing a glycoconjugate;
    incorporating the alkynyl-derivatized sugar into the cell,
        wherein the alkynyl-derivatized sugar is subsequently used by the cell to produce a tagged glycoconjugate;
    wherein the tagged glycoconjugate includes:
        a glycan portion;
        a conjugate portion; and
        an alkynyl functional group; and
    reacting the tagged glycoconjugate with a probe to produce a labeled, tagged glycoconjugate;
        wherein the resultant toxicity of the method is decreased by at least 10% as compared to presenting an azido-derivatized sugar to a cell to produce the tagged glycoconjugate.
46. The method of claim 45 wherein the resultant toxicity is decreased by at least 50%.
47. A method comprising the steps of:
    presenting an alkynyl-derivatized sugar to a cell,
        wherein the alkynyl-derivatized sugar has an alkynyl functional group, and wherein the cell is capable of producing a glycoconjugate;
    incorporating the alkynyl-derivatized sugar into the cell, wherein the alkynyl-derivatized sugar is subsequently used by the cell to produce a tagged glycoconjugate;
wherein the tagged glycoconjugate includes
a glycan portion;
a conjugate portion; and
an alkynyl functional group;
reacting the tagged glycoconjugate with a probe to produce a labeled, tagged glycoconjugate;
detecting the labeled glycoconjugate; and
differentially analyzing the proteomes of the cells incorporating detected, labeled glycoconjugate.

48. The method of claim 47, where the cells are H. pylori or H. pylori-infected cells.

49. A method comprising the steps of:
providing an alkynyl-derivatized sugar to a cell population, wherein the alkynyl-derivatized sugar has an alkynyl functional group, and
wherein the cells are capable of producing a glycoconjugate;
incorporating the alkynyl-derivatized sugar into the cells;
wherein the alkynyl-derivatized sugar is subsequently used by the cells to produce a tagged glycoconjugate;
wherein the tagged glycoconjugate includes a glycan portion;
a conjugate portion; and
an alkynyl functional group;
reacting the tagged glycoconjugate with a probe to produce a labeled, tagged glycoconjugate;
visualizing the labeled, tagged glycoconjugate population of the cells; and
differentially analyzing the subset of cells expressing labeled, tagged Lewis antigen epitopes.

50. The method of claim 49, further comprising generating antibodies to the subset of cells expressing Lewis antigen epitopes.

51. The method of claim 2, wherein the cells are presented with derivatized sugars for a limited period of time.

52. The method of claim 51, wherein the limited period of time is 30 minutes.

53. The method of claim 51, wherein the derivatized sugars are presented to a cell for a limited time, and the presenting step is succeeded by presenting the cell with non-derivatized sugars.

54. The method of claim 51, wherein the derivatized sugars are presented to a cell for a limited time, and both preceded and succeeded by presenting the cell with non-derivatized sugars.

55. The method of claim 51, wherein the derivatized sugars are subsequently labeled and detected at various time intervals subsequent to the limited presentment of such sugars to the cell.

56. The method of claim 51, wherein various time interval detections of derivatized sugars are compared so as to assess cellular trafficking of glycoconjugates.

57. The method of claim 56, wherein differential cellular trafficking of glycoconjugates is assessed.

58. The method of claim 56, wherein the various time interval detections of derivatized sugars are compared with various interval detections of the location of various intracellular and extracellular bodies so as to assess differential cellular trafficking of glycoconjugates.

59. The method of claim 51, wherein the derivatized sugars that are presented to a cell for a limited time are alkynyl-derivatized sugars.

60. The method of claim 51, wherein the derivatized sugars that are presented to a cell for a limited time are azido-derivatized sugars.

61. The method of claim 51, wherein the derivatized sugars that are presented to a cell for a limited time are both alkynyl and azido-derivatized sugars.

62. The method of claim 51, wherein the derivatized sugars that are presented to a cell for a limited time are incorporated into fucosylated glycoconjugates.

63. The method of claim 51, wherein the derivatized sugars that are presented to a cell for a limited time are incorporated into sialylated glycoconjugates.

64. The method of claim 53, wherein the derivatized sugars that are presented to a cell for a limited time and are preceded and succeeded by presenting the cell with non-derivatized sugars are incorporated into both fucosylated and sialylated glycoconjugates.

* * * * *